US011260048B2

(12) United States Patent
Ng et al.

(10) Patent No.: US 11,260,048 B2
(45) Date of Patent: Mar. 1, 2022

(54) COMPOUNDS AND COMPOSITIONS FOR INHIBITING RETINAL PIGMENT EPITHELIUM DEGENERATION AND METHODS USING THE SAME

(71) Applicant: The Schepens Eye Research Institute, Inc., Boston, MA (US)

(72) Inventors: Yin Shan Eric Ng, North Billerica, MA (US); Gopalan Gnanaguru, Cambridge, MA (US); Ashley Mackey, Somerville, MA (US); Patricia A. D'Amore, Newton, MA (US); David Scott, Newton, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 16/652,909

(22) PCT Filed: Oct. 3, 2018

(86) PCT No.: PCT/US2018/054258
§ 371 (c)(1),
(2) Date: Apr. 1, 2020

(87) PCT Pub. No.: WO2019/070917
PCT Pub. Date: Apr. 11, 2019

(65) Prior Publication Data
US 2020/0316032 A1    Oct. 8, 2020

Related U.S. Application Data

(60) Provisional application No. 62/568,159, filed on Oct. 4, 2017, provisional application No. 62/567,651, filed on Oct. 3, 2017.

(51) Int. Cl.
| | |
|---|---|
| *A61K 31/427* | (2006.01) |
| *A61K 31/05* | (2006.01) |
| *A61K 31/085* | (2006.01) |
| *A61K 31/167* | (2006.01) |
| *A61K 31/352* | (2006.01) |
| *A61K 31/4155* | (2006.01) |
| *A61K 31/4196* | (2006.01) |
| *A61K 31/422* | (2006.01) |
| *A61K 31/4245* | (2006.01) |
| *A61K 31/496* | (2006.01) |
| *A61K 31/498* | (2006.01) |
| *A61K 31/5377* | (2006.01) |
| *A61K 9/00* | (2006.01) |

(52) U.S. Cl.
CPC ............ *A61K 31/427* (2013.01); *A61K 31/05* (2013.01); *A61K 31/085* (2013.01); *A61K 31/167* (2013.01); *A61K 31/352* (2013.01); *A61K 31/4155* (2013.01); *A61K 31/4196* (2013.01); *A61K 31/422* (2013.01); *A61K 31/4245* (2013.01); *A61K 31/496* (2013.01); *A61K 31/498* (2013.01); *A61K 31/5377* (2013.01); *A61K 9/0019* (2013.01); *A61K 9/0051* (2013.01)

(58) Field of Classification Search
CPC ............................... A61K 31/427; A61K 31/05
See application file for complete search history.

(56) References Cited

U.S. PATENT DOCUMENTS

| | | |
|---|---|---|
| 4,237,140 A | 12/1980 | Dudzinski |
| 4,309,404 A | 1/1982 | Deneale et al. |
| 4,309,406 A | 1/1982 | Guley et al. |
| 4,521,210 A | 6/1985 | Wong |
| 4,556,552 A | 12/1985 | Porter et al. |
| 4,704,295 A | 11/1987 | Porter et al. |
| 4,853,224 A | 8/1989 | Wong |
| 4,861,760 A | 8/1989 | Mazuel et al. |
| 4,911,920 A | 3/1990 | Jani et al. |
| 4,997,652 A | 3/1991 | Wong |
| 5,164,188 A | 11/1992 | Wong |
| 5,212,162 A | 5/1993 | Missel et al. |
| 5,279,834 A | 1/1994 | Meybeck |
| 5,403,841 A | 4/1995 | Lang et al. |
| 5,443,505 A | 8/1995 | Wong et al. |
| 5,501,856 A | 3/1996 | Ohtori et al. |
| 5,641,750 A | 6/1997 | Louis |
| 5,731,005 A | 3/1998 | Ottoboni et al. |
| 5,766,242 A | 6/1998 | Wong et al. |
| 5,824,072 A | 10/1998 | Wong |
| 5,837,226 A | 11/1998 | Jungherr et al. |

(Continued)

FOREIGN PATENT DOCUMENTS

| | | |
|---|---|---|
| WO | 79000556 A1 | 8/1979 |
| WO | 9605309 A2 | 2/1996 |

(Continued)

OTHER PUBLICATIONS

Pubmed Compound Summary for CID 785, "Hydroquinone", U.S. National Library of Medicine, Sep. 16, 2004 (Sep. 16, 2004), p. 1; p. 1 (https://pubchem.ncbi.nlm.nih.gov/compound/Hydroquinone) (77 pages).

(Continued)

*Primary Examiner* — Kamal A Saeed
(74) *Attorney, Agent, or Firm* — Mintz Levin Cohn Ferris Glovsky and Popeo, P.C.; Ingrid A. Beattie; Joohee Lee

(57) ABSTRACT

There are provided inter alia compounds capable of inhibiting retinal pigment epithelium (RPE) degeneration or geography atrophy (GA) associated with age-related macular degeneration (AMD), and methods of using the same.

13 Claims, 11 Drawing Sheets

(56) References Cited

U.S. PATENT DOCUMENTS

| | | | |
|---|---|---|---|
| 5,869,079 | A | 2/1999 | Wong et al. |
| 6,074,661 | A | 6/2000 | Olejnik et al. |
| 6,331,313 | B1 | 12/2001 | Wong et al. |
| 6,369,116 | B1 | 4/2002 | Wong et al. |
| 6,699,493 | B2 | 3/2004 | Wong |
| 7,354,574 | B2 | 4/2008 | Peyman |
| 8,293,210 | B2 | 10/2012 | Huang et al. |
| 9,737,496 | B2 * | 8/2017 | Scott .................. C07C 217/64 |
| 2005/0043410 | A1 | 2/2005 | Brazzell et al. |
| 2008/0131484 | A1 | 6/2008 | Robinson et al. |
| 2009/0326074 | A1 | 12/2009 | Scott et al. |
| 2011/0269689 | A1 | 11/2011 | Yu |
| 2013/0109759 | A1 | 5/2013 | Miller |

FOREIGN PATENT DOCUMENTS

| | | |
|---|---|---|
| WO | 2016190852 A1 | 12/2016 |
| WO | 2019070917 A1 | 4/2019 |

OTHER PUBLICATIONS

Written Opinion of the International Searching Authority for International Patent Application No. PCT/US2018/054258 dated Jan. 31, 2019 (7 pages).

International Search Report for International Patent Application No. PCT/US2018/054258 dated Jan. 31, 2019 (3 pages.

Abais et al. (May 1, 2015) "Redox Regulation of NLRP3 Inflammasomes: ROS as Trigger or Effector?", Antioxid Redox Signal, 22(13):1111-1129.

Babich H. (Oct. 1982) "Butylated Hydroxytoluene (BHT): A Review", Environmental Research, 29(1):1-29.

Barbosa et al. (Apr. 2014) "Age-related macular degeneration and protective effect of HMG Co-A reductase inhibitors (statins): results from the National Health and Nutrition Examination Survey 2005-2008", Eye (Lond), 28(4):472-480.

Berge et al. (Jan. 1977) "Pharmaceutical Salts", Journal of Pharmaceutical Sciences, 66(1):1-19.

Biewenga et al. (Sep. 1997) "The Pharmacology of the Antioxidant Lipoic Acid", General Pharmacology, 29(3):315-331.

Chen et al. (Apr. 2009) "Dysfunction of the Retinal Pigment Epithelium With Age: Increased Iron Decreases Phagocytosis and Lysosomal Activity", Investigative Ophthalmology & Visual Science, 50(4):1895-1902.

Coll et al. (2015) "A Small-Molecule Inhibitor of the NLRP3 Inflammasome for the Treatment of Inflammatory Diseases", Nature Medicine, 21(3):248-255.

Cos et al. (Sep. 2003) "Comparative Study of Eight Well-Known Polyphenolic Antioxidants", Journal of Pharmacy and Pharmacology, 55(9):1291-1297.

Curcio et al. (Jan. 2001) "Accumulation of Cholesterol with Age in Human Bruch's Membrane", Investigative Ophthalmology & Visual Science, 42(1):265-274.

Curcio et al. (Dec. 2018) "The Oil Spill in Ageing Bruch Membrane", British Journal of Ophthalmology, 95(12):1638-1645.

Ding et al. (2013) "Oxidant Stress in Mitochondrial DNA Damage, Autophagy and Inflammation in Atherosclerosis", Scientific Reports, 3:1077.

Dodd et al. (Dec. 2008) "N-Acetylcysteine for Antioxidant Therapy: Pharmacology and Clinical Utility", Expert Opinion on Biological Therapy, 8(12):1955-1962.

Doyle et al. (May 2012) "NLRP3 Has a Protective Role in Age-Related Macular Degeneration Through The Induction of IL-18 by Drusen Components", Nature Medicine, 18(5):791-798.

Gnanaguru et al. (Sep. 2016) "Oxidized Lipoprotein Uptake Through the CD36 Receptor Activates the NLRP3 Inflammasome in Human Retinal Pigment Epithelial Cells", Investigative Ophthalmology & Visual Science, 57:4704-4712.

Guo et al. (2015) "Inflammasomes: Mechanism of Action, Role in Disease, and Therapeutics", Nature Medicine, 21(7):677-687.

Honda et al. (Dec. 2014) "Isoliquiritigenin is a Potent Inhibitor of NLRP3 Inflammasome Activation and Diet-Induced Adipose Tissue Inflammation", Journal of Leukocyte Biology, 96(6):1087-1100.

Ishida et al. (May 2006) "High density lipoprotein mediated lipid efflux from retinal pigment epithelial cells in culture", British Journal of Ophthalmology, 90(5):616-620.

Ishizaki et al. (Jan. 27, 1997) "Comparison of Various Lazaroid Compounds For Protection Against Ischemic Liver Injury", Transplantation Proceedings, 63(2):202-208.

Jong Paulust. (Oct. 5, 2006) "Age-related macular degeneration", The New England Journal of Medicine, 355(14):1474-1485.

Kikuchi et al. (Jun. 2009) "The Free Radical Scavenger Edaravone Rescues Rats from Cerebral Infarction by Attenuating the Release of High-Mobility Group Box-1 in Neuronal Cells", Journal of Pharmacology and Experimental Therapeutics, 329(3):865-874.

Ledenev et al. (Aug. 1986) "A Simple Assay of the Superoxide Generation Rate With Tiron as an EPR-Visible Radical Scavenger", Biochemistry International, 13(2):391-396.

Leeuwen et al. (Feb. 2003) "Epidemiology of Age-Related Maculopathy: A Review", European Journal of Epidemiology, 18(9):845-854.

Lim et al. (Apr. 2014) "Age-Dependent Increases in Lysosomal pH, Lysosomal Gene Expression and Autofluorescence of Mouse RPE Cells; Parallels With The ABCA4−/− Mice Suggest Causal Factors in Age-Dependent Pathophysiology", Investigative Ophthalmology & Visual Science, 55:2957.

Lu et al. (Nov. 2009) "Lipid Peroxidation Products Reduce Lysosomal Protease Activities in Human Retinal Pigment Epithelial Cells Via Two Different Mechanisms of Action ", Experimental eye Research, 90(2):261-266.

Ludwig Annick (Nov. 3, 2005) "The Use of Mucoadhesive Polymers in Ocular Drug Delivery", Advanced Drug Delivery Reviews, 57(11):1595-1639.

Petrilli et al. (Dec. 2007) "The Inflammasome: A Danger Sensing Complex Triggering Innate Immunity", Current Opinion in Immunology, 19(6):615-622.

Sacconi et al. (2017) "A Review of Current and Future Managementof Geographic Atrophy", Ophthalmology and Therapy, 6(1):69-77.

Wang et al. (Apr. 23, 2010) "Abundant Lipid and Protein Components of Drusen", PLOS One, 12 pages.

Shaw et al. (2016) "Oxidative Stress, Innate Immunity, and Age-Related Macular Degeneration", AIMS Molecular Science, 3(2):196-221.

Sheedy et al. (Aug. 2013) "CD36 Coordinates NLRP3 Inflammasome Activation by Facilitating Intracellular Nucleation of Soluble Ligands Into Particulate Ligands in Sterile Inflammation", Nature Immunology, 14(8):812-820.

Sun et al. (Mar. 2006) "Light-induced oxidation of photoreceptor outer segment phospholipids generates ligands for CD36-mediated phagocytosis by retinal pigment epithelium—A potential mechanism for modulating outer segment phagocytosis under oxidant stress conditons", Journal of Biological Chemistry, 281(7):4222-4230.

Tseng et al. (Jan. 7, 2013) "NLRP3 Inflammasome Activation in Retinal Pigment Epithelial Cells by Lysosomal Destabilization: Implications for Age-Related Macular Degeneration", Investigative Ophthalmology & Visual Science, 54(1):110-120.

Vorobjeva et al. (Feb. 2016) "Effects of the antioxidants Trolox, Tiron and Tempol on neutrophil extracellular trap formation", Immunobiology, 221(2):208-219.

* cited by examiner

IC50 for Trolox: 5.436 μM

COMPOUNDS AND COMPOSITIONS FOR INHIBITING RETINAL PIGMENT EPITHELIUM DEGENERATION AND METHODS USING THE SAME

CROSS-REFERENCES TO RELATED APPLICATIONS

This application is a U.S. national stage application filed under 35 U.S.C. § 371 of International Patent Application No. PCT/US2018/05425, filed Oct. 3, 2018, which claims the benefit of U.S. Provisional Application No. 62/567,651, filed Oct. 3, 2017, and U.S. Provisional Application No. 62/568,159, filed Oct. 4, 2017, which are incorporated herein by reference in their entirety and for all purposes.

BACKGROUND

Geographic atrophy (GA), or late stage dry age-related macular degeneration (AMD), is characterized by degeneration and death of the retinal pigment epithelium (RPE) in the macula, resulting in severe, irreversible vision loss. As there is no established treatment for dry AMD, new therapies are needed. The exact mechanisms underlying pathogenesis of AMD remain unknown.

SUMMARY OF THE INVENTION

Presently, no therapy is approved for the treatment of GA. GA therefore represents an important unmet need in the field of ophthalmology. The invention provides a solution to the problem by providing compounds with a hindered phenol group that are uniquely effective in inhibiting RPE degeneration or GA associated with AMD. The term "hindered phenol" means, unless otherwise stated, a hydroxy-phenyl (phenol) wherein the hydroxy group is flanked by one or two ortho substituent(s), such as, but not limited to, alkyl, or substituted alkyl groups. For example, analogs of drugs such trolox or BHT that contain a hindered phenol are characterized by more potent RPE protective activity compared to the parental compounds. For example, the compounds are at least 10, 20, 50, 100% more potent and even 2×, 3×, 5×, or more potent than the parental compound from which it was derived. The invention features compounds, compositions, and methods for treating RPE degeneration and death (e.g., RPE degeneration and death associated with AM using such compounds. In various embodiments, compounds and compositions provided herein are capable of inhibiting RPE degeneration or GA associated with AMD. The invention encompasses such compounds and compositions for use in treatments for AMD and GA associated with AMD.

In an aspect, provided herein is a method of treating or preventing AMD in a subject, the method comprising administering to the subject an effective amount of a compound having a formula (I): a compound having a formula (I),

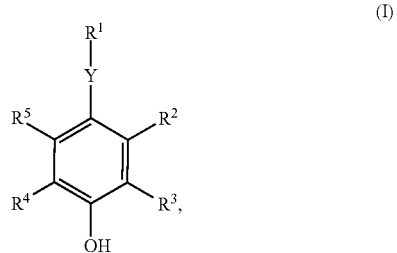

(I)

or a pharmaceutically acceptable salt thereof, and a pharmaceutically acceptable excipient.

Y is —O—, —NR$^{13}$—, or —CR$^{14}$R$^{15}$—. R$^1$ is hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is hydrogen, halogen, —CX$^2_3$, —CHX$^2_2$, —CH$_2$X$^2$, —OCX$^2_3$, —OCH$_2$X$^2$, —OCHX$^2_2$, —CN, —SO$_{n2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is hydrogen, halogen, —CX$^3_3$, —CHX$^3_2$, —CH$_2$X$^3$, —OCX$^3_3$, —OCH$_2$X$^3$, —OCHX$^3_2$, —CN, —SO$_{n3}$R$^{3D}$, —SO$_{v3}$NR$^{3A}$R$^{3B}$, —NHC(O)NR$^{3A}$R$^{3B}$, —N(O)$_{m3}$, —NR$^{3A}$R$^{3B}$, —C(O)R$^{3C}$, —C(O)—OR$^{3C}$, —C(O)NR$^{3A}$R$^{3B}$, —NR$^{3A}$SO$_2$R$^{3D}$, —NR$^{3A}$C(O)R$^{3C}$, —NR$^{3A}$C(O)OR$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is hydrogen, halogen, —CX$^4_3$, —CHX$^4_2$, —CH$_2$X$^4$, —OCX$^4_3$, —OCH$_2$X$^4$, —OCHX$^4_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^5$ is hydrogen, halogen, —CX$^5_3$, —CHX$^5_2$, —CH$_2$X$^5$, —OCX$^5_3$, —OCH$_2$X$^5$, —OCHX$^5_2$, —CN, —SO$_{n5}$R$^{5D}$, —SO$_{v5}$NR$^{5A}$R$^{5B}$, —NHC(O)NR$^{5A}$R$^{5B}$, —N(O)$_{m5}$, —NR$^{5A}$R$^{5B}$, —C(O)R$^{5C}$, —C(O)R$^{5C}$, —C(O)NR$^{5A}$R$^{5B}$, —NR$^{5A}$SO$_2$R$^{5D}$, —NR$^{5A}$C(O)R$^{5C}$, —NR$^{5A}$C(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each R$^{13}$, R$^{14}$ and R$^{15}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, and R$^{5D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^1$ and R$^2$ together with atoms attached thereto are optionally joined to form substituted or unsubstituted cycloalkyl, substituted or unsubstituted heterocycloalkyl, substituted or unsubstituted aryl or substituted or unsubstituted heteroaryl. n1, n2, n3, n4, and n5 are independently an integer from 0 to 4. m1, m2, m3, m4, m5, v1, v2, v3, v4, and v5 are independently an integer from 1 to 2. X, $X^1$, $X^2$, $X^3$, $X^4$, $X^5$, and $X^6$ are independently —F, —Cl, —Br, or —I. or a pharmaceutically acceptable salt thereof.

In an aspect is provided a pharmaceutical composition comprising, consisting essentially of, or consisting of a compound as described herein. In embodiments, the pharmaceutical composition is formulated for ocular administration (e.g., for topical, intravitreal, intracameral, subconjunctival, subtendon, retrobulbar, or posterior juxtascleral administration).

DETAILED DESCRIPTION

I. Definitions

Figure 1:
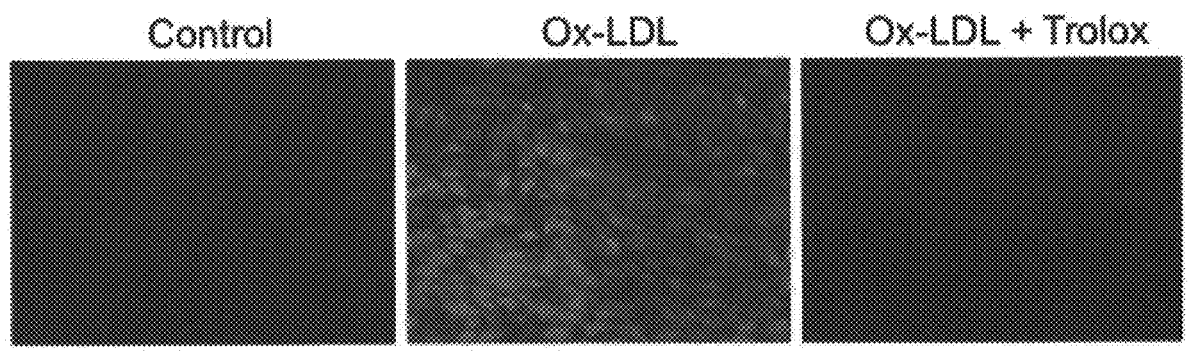
FIG. 1 is a series of images showing that oxidized low-density lipoproteins (ox-LDL) induced reactive oxygen species (ROS) formation in RPE that is suppressed by 6-hydroxy-2,5,7,8-tetramethylchroman-2-carboxylic acid (trolox). Adult retinal pigment epithelium 19 (ARPE-19) cells were treated with 200 µg/ml ox-LDL for 28 hours, with and without trolox. ROS was detected by using the ROS-ID® Total ROS detection kit (Enzo Life Sciences, Inc., Farmingdale, N.Y.).

The abbreviations used herein have their conventional meaning within the chemical and biological arts. The chemical structures and formulae set forth herein are constructed according to the standard rules of chemical valency known in the chemical arts.

As used herein, the term "about" in the context of a numerical value or range means 10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to 5.0 mg.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, or S), and wherein the nitrogen and sulfur atoms may optionally be oxidized, and the nitrogen heteroatom may optionally be quaternized. The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, biphenyl, pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded ("=O") to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

The term "alkylarylene" as an arylene moiety covalently bonded to an alkylene moiety (also referred to herein as an alkylene linker). In embodiments, the alkylarylene group has the formula:

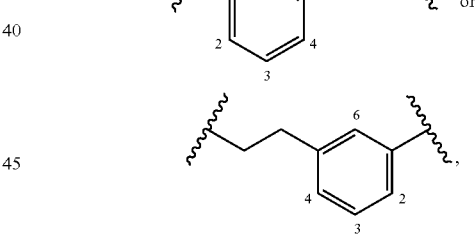

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$ —SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present. The term "hindered phenol" means, unless otherwise stated, a hydroxy-phenyl (phenol) wherein the hydroxy group is flanked by one or two ortho substituent(s), such as, but not limited to, alkyl, or substituted alkyl groups.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group" or "substituent" as used herein, means a group selected from the following moieties:

(A) oxo, halogen, —CF$_3$, —CH$_2$F, —CHF$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CH$_2$F, —CHF$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —OCH$_2$F, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CH$_2$F, —CHF$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)— OH, —NHOH, —OCF$_3$, —OCHF$_2$, —OCH$_2$F, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CH$_2$F, —CHF$_2$, —CN, —OH, —NH$_2$, —COOH, —CONH$_2$, NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —OCH$_2$F, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene.

In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each R position that contains more than one possible constituent. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

The symbol " $\sim\!\!\sim$ " denotes the point of attachment of a chemical moiety to the remainder of a molecule or chemical formula.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

The terms "treating", or "treatment" refers to any indicia of success in the therapy or amelioration of an injury, disease, pathology or condition (e.g., RPE degeneration, AMD, or GA), including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

The term "prevent" refers to a decrease in the occurrence of the disease symptoms (e.g. RPE degeneration, AMD, or GA) in a patient. As indicated above, the prevention may be complete (no detectable symptoms) or partial, such that fewer symptoms are observed than would likely occur absent treatment.

"Patient" or "subject" refers to a living organism who is a member of a species that may suffering from a disease or condition that can be treated by administration of a pharmaceutical composition as provided herein. Non-limiting examples include primates, other mammals, bovines, rats, mice, dogs, monkeys, goat, sheep, cows, deer, and other non-mammalian animals. In some embodiments, a patient is human.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. An individual described as a "subject," "patient," "individual," and the like does not necessarily have a given disease, but may be merely seeking medical advice. The terms "subject," "patient," "individual," and the like as used herein include all members of the animal kingdom that may suffer from the indicated disorder. In some aspects, the subject is a mammal, and in some aspects, the subject is a human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, a "symptom" associated with a disorder includes any clinical or laboratory manifestation associated with the disorder, and is not limited to what the subject can feel or observe.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects.

Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent. In embodiments, the administration is ocular administration, such as topical, intravitreal, intracameral, subconjunctival, subtendon, retrobulbar, or posterior juxtascleral administration.

In various embodiments, a composition comprising a compound disclosed herein may be administered only once or multiple times. For example, a compound may be administered using a method disclosed herein at least about once, twice, three times, four times, five times, six times, or seven times per day week, month, or year. In some embodiments, a composition comprising a compound is administered once per month. In certain embodiments, the composition is administered once per month via intravitreal injection. In various embodiments, such as embodiments involving eye drops, a composition is self-administered.

In some embodiments, a compound (e.g., a pharmaceutical composition comprising the compound) may be administered locally, e.g., as a topical eye drop, periocular injection (e.g., subtenon), intraocular injection, intravitreal injection, retrobulbar injection, intraretinal injection, subconjunctival injection, or using iontophoresis, or periocular devices which can actively or passively deliver a compound.

Sustained release of a compound may be achieved by the use of technologies such as implants (e.g., solid implants) (which may or may not be bio-degradable) or biodegradable polymeric matrices (e.g., microparticles). These may be administered, e.g., periocularly or intravitreally.

Pharmaceutical formulations adapted for topical administration may be formulated as, e.g., aqueous solutions, ointments, creams, suspensions, lotions, powders, solutions, pastes, gels, sprays, aerosols, liposomes, microcapsules, microspheres, or oils.

For treatments of the eye or other external tissues, such as the mouth or skin, the formulations (e.g., a pharmaceutical composition comprising a compound described herein) may be applied as a topical ointment or cream. When formulated in an ointment, a compound may be employed with either a paraffinic or a water-miscible ointment base. Alternatively, a compound may be formulated in a cream (such as an emulsion, e.g., an oil-in-water emulsion or a water-in-oil emulsion).

Pharmaceutical formulations adapted for topical administrations to the eye include eye drops wherein a compound is dissolved or suspended in a suitable carrier, especially an aqueous solvent. Formulations to be administered to the eye will have ophthalmically compatible pH and osmolality.

The term "ophthalmically acceptable vehicle," "ophthalmologically acceptable vehicle," and the like mean a pharmaceutical composition having physical properties (e.g., pH and/or osmolality) that are physiologically compatible with ophthalmic tissues.

In some embodiments, an ophthalmic composition (e.g, a composition comprising a compound disclosed herein and an ophthalmologically acceptable vehicle) of the present invention is formulated as sterile aqueous solutions having an osmolality of from about 200 to about 400 milliosmoles/kilogram water ("mOsm/kg") and a physiologically compatible pH. The osmolality of the solutions may be adjusted by means of conventional agents, such as inorganic salts (e.g., NaC), organic salts (e.g., sodium citrate), polyhydric alcohols (e.g., propylene glycol or sorbitol) or combinations thereof.

In various embodiments, the ophthalmic formulations (e.g, a composition comprising a compound disclosed herein and an ophthalmologically acceptable vehicle) may be in the form of liquid, solid or semisolid dosage form. The ophthalmic formulations may comprise, depending on the final dosage form, suitable ophthalmically acceptable excipients. In some embodiments, the ophthalmic formulations are formulated to maintain a physiologically tolerable pH range. In certain embodiments, the pH range of the ophthalmic formulation is in the range of from about 5 to about 9. In some embodiments, pH range of the ophthalmic formulation is in the range of from about 6 to about 8, or is about 6.5, about 7, or about 7.5.

In some embodiments, the composition is in the form of an aqueous solution, such as one that can be presented in the form of eye drops. By means of a suitable dispenser, a desired dosage of the active agent can be metered by administration of a known number of drops into the eye, such as by one, two, three, four, or five drops.

One or more ophthalmically acceptable pH adjusting agents and/or buffering agents can be included in a composition, including acids such as acetic, boric, citric, lactic, phosphoric, and hydrochloric acids; bases such as sodium hydroxide, sodium phosphate, sodium borate, sodium citrate, sodium acetate, and sodium lactate; and buffers such as citrate/dextrose, sodium bicarbonate, and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium, or ammonium cations and chloride, citrate, ascorbate, borate, phosphate, bicarbonate, sulfate, thiosulfate, or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g., poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition, and polymeric coatings that will enhance drug diffusion, erosion, dissolution, and osmosis.

Formulations for drug delivery using ocular devices may combine one or more active agents and adjuvants appropriate for the indicated route of administration. For example, a compound described herein (optionally with another agent) may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers, and a carrier or diluent that has a time delay property. Representative examples of biodegradable compositions can include albumin, gelatin, starch, cellulose, dextrans, polysaccharides, poly (D,L-lactide), poly (D,L-lactide-co-glycolide), poly (glycolide), poly (hydroxybutyrate), poly (alkylcarbonate) and poly (orthoesters), and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig, Adv. Drug Deliv. Rev. 3; 57:1595-639 (2005), the entire content of which is incorporated herein by reference.

Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661;

6,331,313; 6,369,116; 6,699,493; and 8,293,210, the entire contents of each of which are incorporated herein by reference.

The implants may be monolithic, i.e. having the active agent (e.g., a compound described herein) or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including a compound described herein, may be distributed in a non-homogenous pattern in the matrix. For example, the implant may include a portion that has a greater concentration of the compound relative to a second portion of the implant.

In various embodiments, the intraocular implants disclosed herein may have a size of between about 5 um and about 2 mm, or between about 10 um and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. In some embodiments, the implant may be a cylindrical pellet (e.g., a rod) with dimensions of about 2 mm×0.75 mm diameter. In certain embodiments, the implant may be a cylindrical pellet with a length of about 7 mm to about 10 mm, and a diameter of about 0.75 mm to about 1.5 mm.

In various embodiments, the implants may also be at least somewhat flexible so as to facilitate both insertion of the implant in the eye, such as in the vitreous, and accommodation of the implant. The total weight of the implant is usually about 250-5000 µg, more preferably about 500-1000 µg. For example, an implant may be about 500 g, or about 1000 µg. For non-human subject, the dimensions and total weight of the implant(s) may be larger or smaller, depending on the type of subject. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques, and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of 0.5 µm to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Microspheres for ocular delivery are described, for example, in U.S. Pat. Nos. 5,837,226; 5,731,005; 5,641,750; 7,354,574; and U.S. Pub. No. 2008-0131484, the entire contents of each of which are incorporated herein by reference.

In various embodiments comprising oral or enteral formulations, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. Nos. 4,704,295; 4,556,552; 4,309,404; and 4,309,406, the entire contents of each of which are incorporated herein by reference.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity or level of a protein in the absence of a compound as described herein (including embodiments and examples). In some embodiments, a control is the measurement of an effect or symptom in the absence of a compound as described herein.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

II. Pharmaceutical Compositions

In one aspect is provided a pharmaceutical composition including a compound, or a salt thereof, and a pharmaceutically acceptable excipient thereof. The compound of the invention is capable of inhibiting retinal pigment epithelium (RPE) degeneration or geography atrophy (GA) associated with age-related macular degeneration (AMD). The compound may have a formula (I),

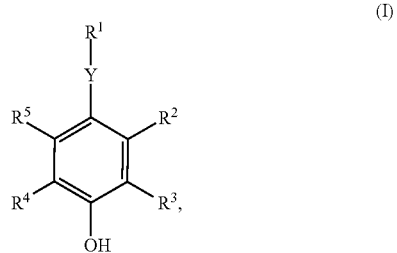

or a pharmaceutically acceptable salt thereof.

In formula (I), Y is —O—, —NR$^{13}$—, or —CR$^{14}$R$^{15}$—. R$^1$ is hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$O R$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is hydrogen, halogen, —CX$^2_3$, —CHX$^2_2$, —CH$_2$X$^2$, —OCX$^2_3$, —OCH$_2$X$^2$, —OCHX$^2_2$, —CN, —SO$_{n2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is hydrogen, halogen, —CX$^3_3$, —CHX$^3_2$, —CH$_2$X$^3$, —OCX$^3_3$, —OCH$_2$X$^3$, —OCHX$^3_2$, —CN, —SO$_{n3}$R$^{3D}$, —SO$_{v3}$NR$^{3A}$R$^{3B}$, —NHC(O)NR$^{3A}$R$^{3B}$, —N(O)$_{m3}$, —NR$^{3A}$R$^{3B}$, —C(O)R$^{3C}$, —C(O)—OR$^{3C}$, —C(O)NR$^{3A}$R$^{3B}$, —NR$^{3A}$SO$_2$R$^{3D}$, —NR$^{3A}$C(O)R$^{3C}$, —NR$^{3A}$C(O)OR$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is hydrogen, halogen, —CX$^4_3$, —CHX$^4_2$, —CH$_2$X$^4$, —OCX$^4_3$, —OCH$_2$X$^4$, —OCHX$^4_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^5$ is hydrogen, halogen, —CX$^5_3$, —CHX$^5_2$, —CH$_2$X$^5$, —OCX$^5_3$, —OCH$_2$X$^5$, —OCHX$^5_2$, —CN, —SO$_{n5}$R$^{5D}$, —SO$_{v5}$NR$^{5A}$R$^{5B}$, —NHC(O)NR$^{5A}$R$^{5B}$, —N(O)$_{m5}$, —NR$^{5A}$R$^{5B}$, —C(O)R$^{5C}$, —C(O)—OR$^{5C}$, —C(O)NR$^{5A}$R$^{5B}$, —NR$^{5A}$SO$_2$R$^{5D}$, —NR$^{5A}$C(O)R$^{5C}$, —NR$^{5A}$C(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each R$^{13}$, R$^{14}$ and R$^{15}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each R$^{1A}$, R$^{1B}$, R$^{1C}$, R$^{1D}$, R$^{2A}$, R$^{2B}$, R$^{2C}$, R$^{2D}$, R$^{3A}$R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, and R$^{5D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^1$ and R$^2$ together with atoms attached thereto are optionally joined to form substituted or unsubstituted cycloalkyl, substituted or unsubstituted heterocycloalkyl, substituted or unsubstituted aryl or substituted or unsubstituted heteroaryl. n1, n2, n3, n4, n5 are independently an integer from 0 to 4. m1, m2, m3, m4, m5, v1, v2, v3, v4, and v5 are independently an integer from 1 to 2. X, X$^1$, X$^2$, X$^3$, X$^4$, and X$^5$ are independently —F, —Cl, —Br, or —I. In some embodiments, provided that when Y is —NH—, then R$^1$ is not hydrogen.

In embodiments, the compound does not have a structure of

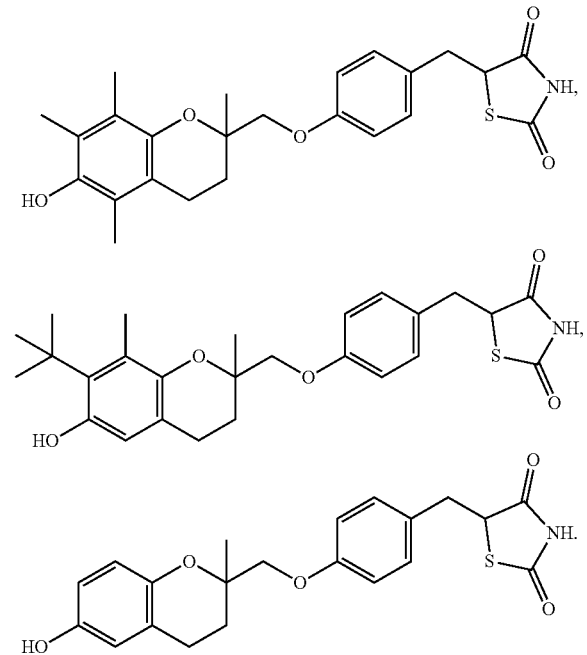

In embodiments, R$^{13}$ is hydrogen, or unsubstituted C$_1$-C$_4$ alkyl. In embodiment, R$^{13}$ is hydrogen. In embodiments, R$^{13}$ is unsubstituted C$_1$-C$_4$ alkyl. In embodiments, R$^{13}$ is methyl. In embodiments, R$^{13}$ is ethyl. In embodiments, R$^{13}$ is propyl. In embodiments, R$^{13}$ is isopropyl. In embodiments, R$^{13}$ is butyl. In embodiments, R$^{13}$ is t-butyl. In embodiments, R$^{13}$ is 1-methylpropyl. In embodiments, R$^{13}$ is 2-methylpropyl.

In embodiments, R$^{14}$ is hydrogen, or unsubstituted C$_1$-C$_4$ alkyl. In embodiment, R$^{14}$ is hydrogen. In embodiments, R$^{14}$ is unsubstituted $C_1$-$C_4$ alkyl. In embodiments, $R^{14}$ is methyl. In embodiments, $R^{14}$ is ethyl. In embodiments, $R^{14}$ is propyl. In embodiments, $R^{14}$ is isopropyl. In embodiments, $R^{14}$ is butyl. In embodiments, $R^{14}$ is t-butyl. In embodiments, $R^{14}$ is 1-methylpropyl. In embodiments, $R^{14}$ is 2-methylpropyl.

In embodiments, $R^{15}$ is hydrogen, or unsubstituted $C_1$-$C_4$ alkyl. In embodiment, $R^{15}$ is hydrogen. In embodiments, $R^{15}$ is unsubstituted $C_1$-$C_4$ alkyl. In embodiments, $R^{15}$ is methyl. In embodiments, $R^{15}$ is ethyl. In embodiments, $R^{15}$ is propyl. In embodiments, $R^{15}$ is isopropyl. In embodiments, $R^{15}$ is butyl. In embodiments, $R^{15}$ is t-butyl. In embodiments, $R^{15}$ is 1-methylpropyl. In embodiments, $R^{15}$ is 2-methylpropyl.

In embodiments, Y is —NH—. In embodiments, $R^1$ is —C(O)$R^{1C}$. In embodiments, $R^1$ is-C(O)H. In embodiments, $R^1$ is —C(O)$CH_3$. In embodiments, $R^1$ is —C(O)$CH_2CH_3$. In embodiments, $R^1$ is —C(O)$CH_2CH_2CH_3$. In embodiments, $R^1$ is —C(O)CH($CH_3$)$_2$. In embodiments, $R^1$ is —C(O)$CH_2CH_2CH_2CH_3$. In embodiments, $R^1$ is —C(O)C($CH_3$)$_3$. In embodiments, $R^1$ is —C(O)$CH_2CH_2CH_2CH_3$.

In embodiments, Y is —O—. In embodiments, $R^1$ is hydrogen, or substituted or unsubstituted $C_1$-$C_6$ alkyl. In embodiments, $R^1$ is substituted or unsubstituted $C_1$-$C_4$ alkyl. In embodiments, $R^1$ is unsubstituted $C_1$-$C_4$ alkyl. In embodiments, $R^1$ is methyl. In embodiments, $R^1$ is ethyl. In embodiments, $R^1$ is propyl. In embodiments, $R^1$ is isopropyl. In embodiments, $R^1$ is butyl. In embodiments, $R^1$ is t-butyl. In embodiments, $R^1$ is 2-methylpropyl. In embodiments, $R^1$ is 1-methylpropyl.

In embodiments, $R^2$ and $R^5$ are hydrogen, or substituted or unsubstituted $C_1$-$C_4$ alkyl. In embodiments, $R^2$ is hydrogen or unsubstituted $C_1$-$C_4$ alkyl. In embodiments, $R^5$ is hydrogen or unsubstituted $C_1$-$C_4$ alkyl. In embodiments, $R^2$ is hydrogen. In embodiments, $R^2$ is methyl. In embodiments, $R^2$ is ethyl. In embodiments, $R^2$ is propyl. In embodiments, $R^2$ is isopropyl. In embodiments, $R^2$ is butyl. In embodiments, $R^2$ is t-butyl. In embodiments, $R^2$ is 1-methylpropyl. In embodiments, $R^2$ is 2-methylpropyl. In embodiments, $R^5$ is hydrogen. In embodiments, R is methyl. In embodiments, $R^5$ is ethyl. In embodiments, $R^5$ is propyl. In embodiments, R is isopropyl. In embodiments, R is butyl. In embodiments, $R^5$ is t-butyl. In embodiments, $R^5$ is 1-methylpropyl. In embodiments, $R^5$ is 2-methylpropyl. $R^2$ and R are hydrogen.

In embodiments, $R^3$ and $R^4$ are independently hydrogen, or substituted or unsubstituted $C_1$-$C_4$ alkyl. In embodiments, $R^3$ and $R^4$ are independently substituted or unsubstituted $C_1$-$C_4$ alkyl. In embodiments, $R^3$ is unsubstituted $C_1$-$C_4$ alkyl. In embodiments, $R^3$ is methyl. In embodiments, $R^3$ is ethyl. In embodiments, $R^3$ is propyl. In embodiments, $R^3$ is isopropyl. In embodiments, $R^3$ is butyl. In embodiments, $R^3$ is t-butyl. In embodiments, $R^3$ is 1-methylpropyl. In embodiments, $R^3$ is 2-methylpropyl. In embodiments, $R^3$ is substituted $C_1$-$C_4$ alkyl. In embodiments, $R^3$ is substituted methyl. In embodiments, $R^3$ is substituted ethyl. In embodiments, $R^3$ is

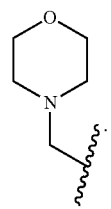 [SMILES: *CN1CCOCC1]

In embodiments, $R^4$ is unsubstituted $C_1$-$C_4$ alkyl. In embodiments, $R^4$ is methyl. In embodiments, $R^4$ is ethyl. In embodiments, $R^4$ is propyl. In embodiments, $R^4$ is isopropyl. In embodiments, $R^4$ is butyl. In embodiments, $R^4$ is t-butyl. In embodiments, $R^4$ is 1-methylpropyl. In embodiments, $R^4$ is 2-methylpropyl. In embodiments, $R^4$ is substituted $C_1$-$C_4$ alkyl. In embodiments, $R^4$ is substituted methyl. In embodiments, $R^4$ is substituted ethyl. In embodiments, $R^4$ is

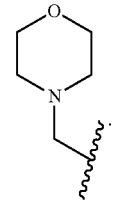 [SMILES: *CN1CCOCC1]

In embodiments, n1 is 0. In embodiments, n1 is 1. In embodiments, n1 is 2. In embodiments, n1 is 3. In embodiments, n1 is 4. In embodiments, m1 is 1. In embodiments, m1 is 2. In embodiments, v1 is 1. In embodiments, v1 is 2. In embodiments, n2 is 0. In embodiments, n2 is 1. In embodiments, n2 is 2. In embodiments, n2 is 3. In embodiments, n2 is 4. In embodiments, m2 is 1. In embodiments, m2 is 2. In embodiments, v2 is 1. In embodiments, v2 is 2. In embodiments, n3 is 0. In embodiments, n3 is 1. In embodiments, n3 is 2. In embodiments, n3 is 3. In embodiments, n3 is 4. In embodiments, m3 is 1. In embodiments, m3 is 2. In embodiments, v3 is 1. In embodiments, v3 is 2. In embodiments, n4 is 0. In embodiments, n4 is 1. In embodiments, n4 is 2. In embodiments, n4 is 3. In embodiments, n4 is 4. In embodiments, m4 is 1. In embodiments, m4 is 2. In embodiments, v4 is 1. In embodiments, v4 is 2. In embodiments, n5 is 0. In embodiments, n5 is 1. In embodiments, n5 is 2. In embodiments, n5 is 3. In embodiments, n5 is 4. In embodiments, m5 is 1. In embodiments, m5 is 2. In embodiments, v5 is 1. In embodiments, v5 is 2.

In embodiments, the compound has a formula (II),

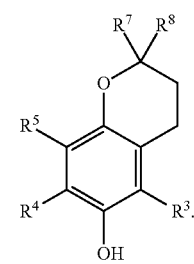

(II)

In formula (II), $R^7$ is hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —NHC(O)$NR^{7A}R^{7B}$, —N(O)$_{m7}$, —$NR^{7A}R^{7B}$, —C(O) $R^{7C}$, —C(O)—$OR^{7C}$, —C(O)$NR^{7A}R^{7B}$, —$OR^{7D}$, —$NR^{7A}SO_2R^{7D}$, —$NR^{7A}$C(O) $R^{7C}$, —$NR^{7A}$C(O)$OR^{7C}$, —$NR^{7A}$O $R^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ is hydrogen, halogen, —$CX^8_3$, —$CHX^8_2$, —$CH_2X^8$, —$OCX^8_3$, —$OCH_2X^8$, —$OCHX^8_2$, —CN, —$SO_{n8}R^{8D}$, —$SO_{v8}NR^{8A}R^{8B}$, —NHC(O)$NR^{8A}R^{8B}$, —N(O)$_{m8}$, —NR$^{8A}$R$^{8B}$, —C(O)R$^{8C}$, —C(O)—OR$^{8C}$, —C(O)NR$^{8A}$R$^{8B}$, —OR$^{8D}$, —NR$^{8A}$SO$_2$R$^{8D}$, —NR$^{8A}$C(O)R$^{8C}$, —NR$^{8A}$C(O)OR$^{8C}$, —NR$^{8A}$ OR$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each R$^{7A}$, R$^{7B}$, R$^{7C}$, R$^{7D}$, R$^{8A}$, R$^{8B}$, R$^{8C}$ and R$^{8D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n7 and n8 are independently an integer from 0 to 4. m7, m8, v7 and v8 are independently an integer from 1 to 2. X$^7$, and X$^8$ are independently —F, —Cl, —Br, or —I.

In embodiments, R$^7$ is hydrogen, or unsubstituted C$_1$-C$_4$ alkyl. In embodiment, R$^7$ is hydrogen. In embodiments, R$^7$ is unsubstituted C$_1$-C$_4$ alkyl. In embodiments, R$^7$ is methyl. In embodiments, R$^7$ is ethyl. In embodiments, R$^7$ is propyl. In embodiments, R$^7$ is isopropyl. In embodiments, R$^7$ is butyl. In embodiments, R$^7$ is t-butyl. In embodiments, R$^7$ is 1-methylpropyl. In embodiments, R$^7$ is 2-methylpropyl.

In embodiments, R$^8$ is represented as:

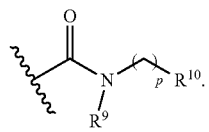

p is an integer from 0 to 4. Each R$^9$ and R$^{10}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^9$ and R$^{10}$ together with atoms attached thereto are optionally joined to form substituted or unsubstituted cycloalkyl, substituted or unsubstituted heterocycloalkyl, substituted or unsubstituted aryl or substituted or unsubstituted heteroaryl. X is as described above.

In embodiments, R$^9$ is hydrogen or unsubstituted C$_1$-C$_4$ alkyl.

In embodiments, R$^9$ is hydrogen, or unsubstituted C$_1$-C$_4$ alkyl. In embodiment, R$^9$ is hydrogen. In embodiments, R$^9$ is unsubstituted C$_1$-C$_4$ alkyl. In embodiments, R$^9$ is methyl. In embodiments, R$^9$ is ethyl. In embodiments, R$^9$ is propyl. In embodiments, R$^9$ is isopropyl. In embodiments, R$^9$ is butyl. In embodiments, R$^9$ is t-butyl. In embodiments, R$^9$ is 1-methylpropyl. In embodiments, R$^9$ is 2-methylpropyl.

In embodiments, R$^{10}$ is:

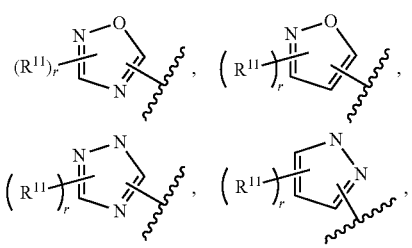

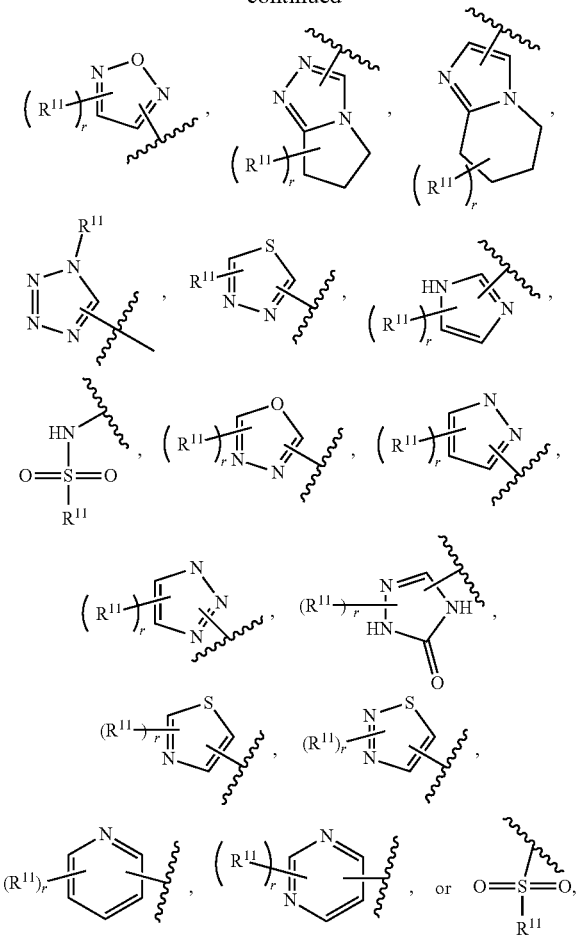

R$^{11}$ is hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —CN, —SO$_{n11}$R$^{11D}$, —SO$_{v11}$NR$^{11A}$R$^{11B}$, —NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O)OR$^{11C}$, —NR$^{11A}$OR$^{11C}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each R$^{11A}$, R$^{11B}$, R$^{11C}$, and R$^{11D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n11 is an integer from 0 to 4. m11 is an integer from 1 to 2. r is an integer from 0 to 9. X$^{11}$ is —F, —Cl, —Br, or —I.

In embodiments, R$^{11}$ is hydrogen, or unsubstituted C$_1$-C$_4$ alkyl. In embodiment, R$^{11}$ is hydrogen. In embodiments, R$^{11}$ is unsubstituted C$_1$-C$_4$ alkyl. In embodiments, R$^{11}$ is methyl. In embodiments, R$^{11}$ is ethyl. In embodiments, R$^{11}$ is propyl. In embodiments, R$^{11}$ is isopropyl. In embodiments, R$^{11}$ is butyl. In embodiments, R$^{11}$ is t-butyl. In embodiments, R$^{11}$ is 1-methylpropyl. In embodiments, R$^{11}$ is 2-methylpropyl.

In embodiments, R$^9$ and R$^{10}$ together with the nitrogen attached thereto are joined to form:

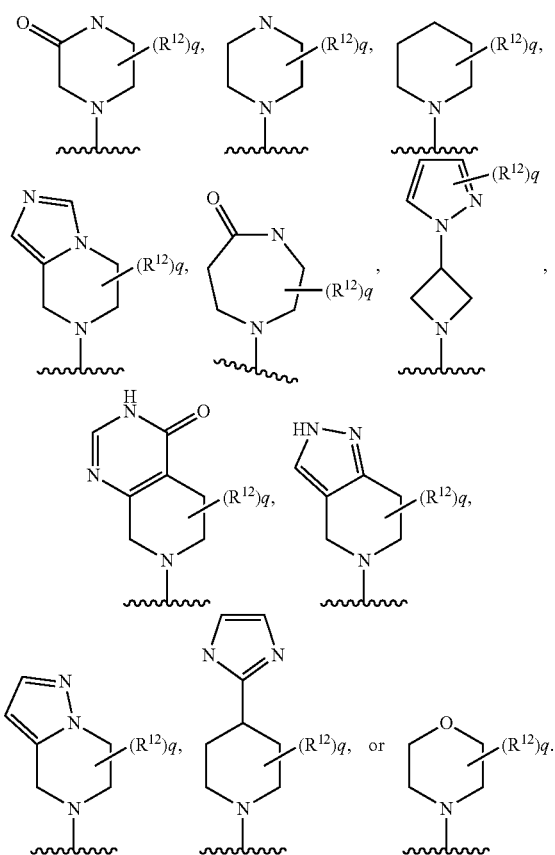

$R^{12}$ is hydrogen, halogen, $-CX^{12}{}_3$, $-CHX^{12}{}_2$, $-CH_2X^{12}$, $-OCX^{12}{}_3$, $-OCH_2X^{12}$, $-OCHX^{12}{}_2$, $-CN$, $-SO_{n12}R^{12D}$, $-SO_{v12}NR^{12A}R^{12B}$, $-NHC(O)NR^{12A}R^{12B}$, $-N(O)_{m12}$, $-NR^{12A}R^{12B}$, $-C(O)R^{12C}$, $-C(O)-OR^{12C}$, $-C(O)NR^{12A}R^{12B}$, $-OR^{12D}$, $-NR^{12A}SO_2R^{12D}$, $-NR^{12A}C(O)R^{12C}$, $-NR^{12A}C(O)OR^{12C}$, $-NR^{12A}OR^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^{12A}$, $R^{12B}$, $R^{12C}$, and $R^{12D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n12 is an integer from 0 to 4. m12 is an integer from 1 to 2. q is an integer from 0 to 6. $X^{12}$ is $-F$, $-Cl$, $-Br$, or $-I$.

In embodiments, $R^{12}$ is hydrogen, unsubstituted $C_1$-$C_4$ alkyl, $-OH$, $-OCH_3$, $-CH_2OH$ or $-CH_2CH_2OH$. In embodiments, $R^{12}$ is hydrogen, or unsubstituted $C_1$-$C_4$ alkyl. In embodiment, $R^{12}$ is hydrogen. In embodiments, $R^{12}$ is unsubstituted $C_1$-$C_4$ alkyl. In embodiments, $R^{12}$ is methyl. In embodiments, $R^{12}$ is ethyl. In embodiments, $R^{12}$ is propyl. In embodiments, $R^{12}$ is isopropyl. In embodiments, $R^{12}$ is butyl. In embodiments, $R^{12}$ is t-butyl. In embodiments, $R^{12}$ is 1-methylpropyl. In embodiments, $R^{12}$ is 2-methylpropyl. In embodiments, $R^{12}$ is $-OH$. In embodiments, $R^{12}$ is $-OCH_3$. In embodiments, $R^{12}$ is $-CH_2OH$. In embodiments, $R^{12}$ is $-CH_2CH_2OH$.

In embodiments, n7 is 0. In embodiments, n7 is 1. In embodiments, n7 is 2. In embodiments, n7 is 3. In embodiments, n7 is 4. In embodiments, m7 is 1. In embodiments, m7 is 2. In embodiments, v7 is 1. In embodiments, v7 is 2. In embodiments, n8 is 0. In embodiments, n8 is 1. In embodiments, n8 is 2. In embodiments, n8 is 3. In embodiments, n8 is 4. In embodiments, m8 is 1. In embodiments, m8 is 2. In embodiments, v8 is 1. In embodiments, v8 is 2. In embodiments, n11 is 0. In embodiments, n11 is 1. In embodiments, n11 is 2. In embodiments, n11 is 3. In embodiments, n11 is 4. In embodiments, m1 is 1. In embodiments, m11 is 2. In embodiments, v11 is 1. In embodiments, v11 is 2. In embodiments, n12 is 0. In embodiments, n12 is 1. In embodiments, n12 is 2. In embodiments, n12 is 3. In embodiments, n12 is 4. In embodiments, m12 is 1. In embodiments, m12 is 2. In embodiments, v12 is 1. In embodiments, v12 is 2.

In embodiments, p is 0. In embodiments, p is 1. In embodiments, p is 2. In embodiments, p is 3. In embodiments, p is 4. In embodiments, r is 0. In embodiments, r is 1. In embodiments, r is 2. In embodiments, r is 3. In embodiments, r is 4. In embodiments, r is 5. In embodiments, r is 6. In embodiments, r is 7. In embodiments, r is 8. In embodiments, r is 9. In embodiments, q is 0. In embodiments, q is 1. In embodiments, q is 2. In embodiments, q is 3. In embodiments, q is 4. In embodiments, q is 5. In embodiments, q is 6.

In embodiments, the compound is:

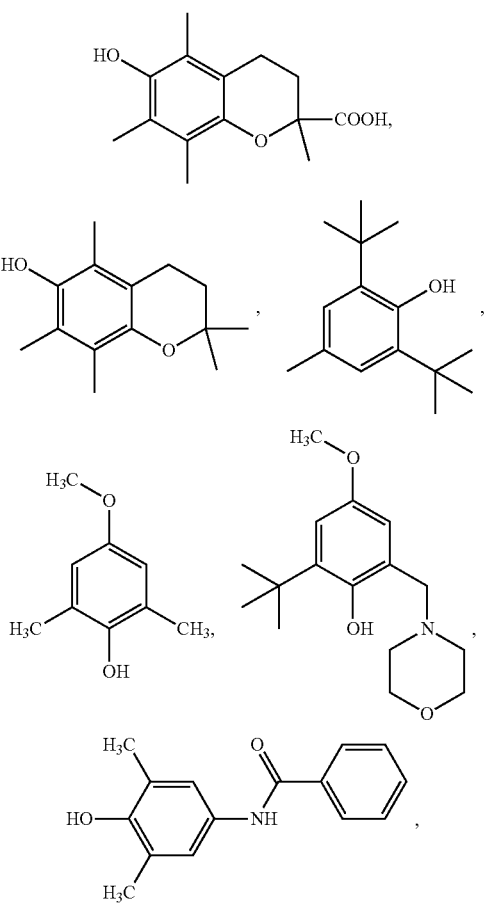

31
-continued
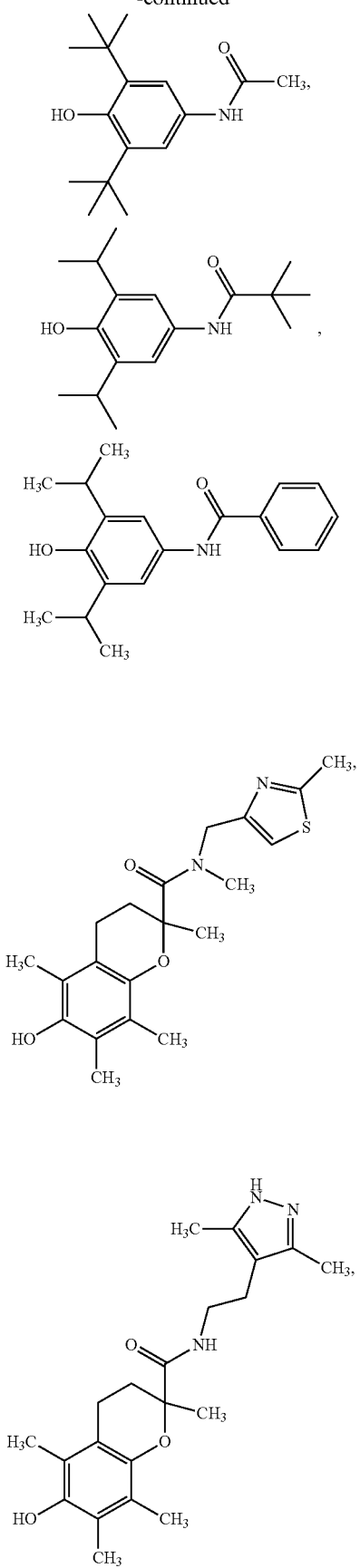
32
-continued
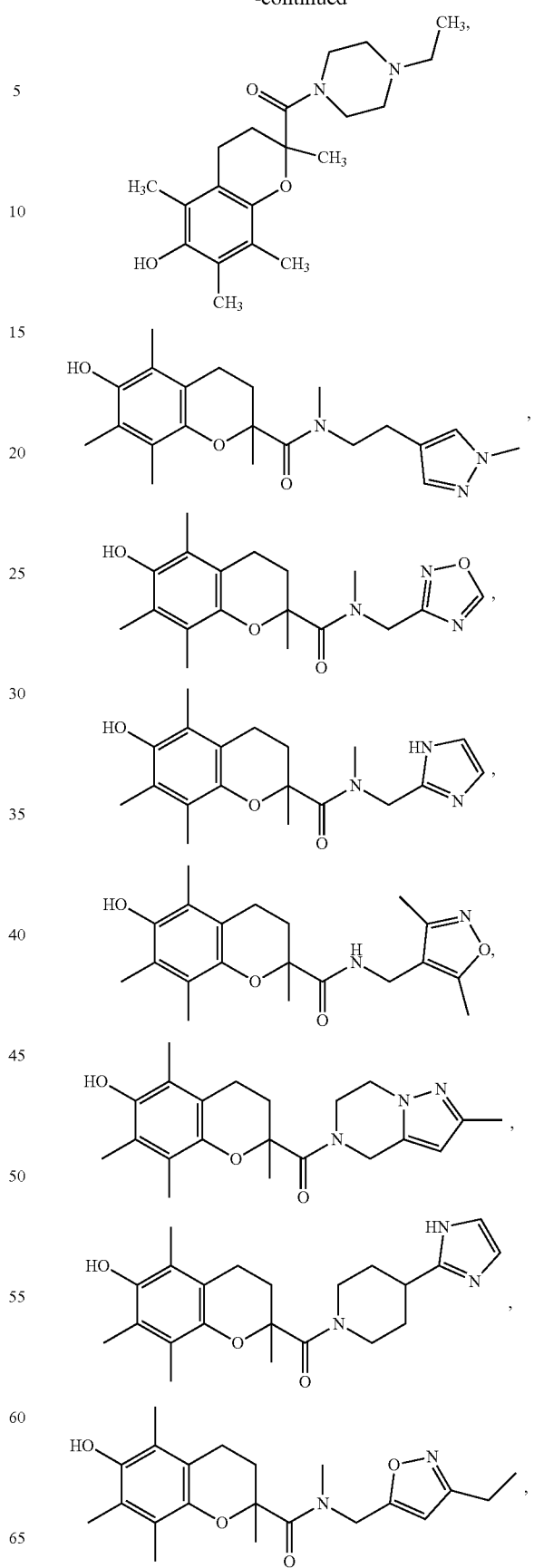

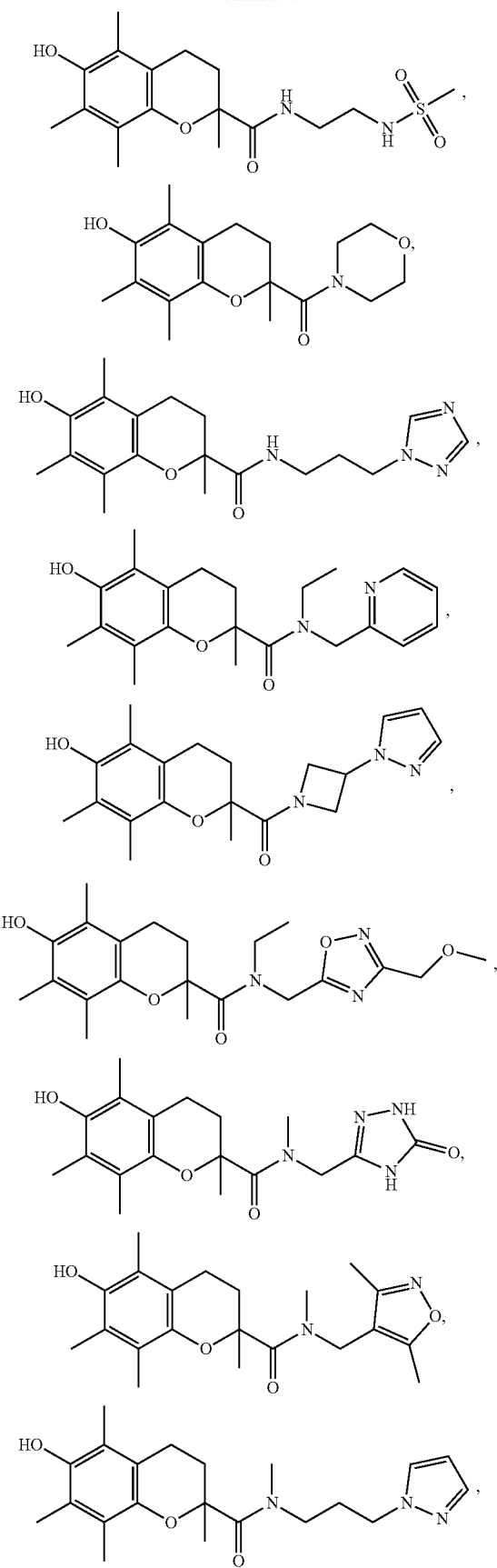

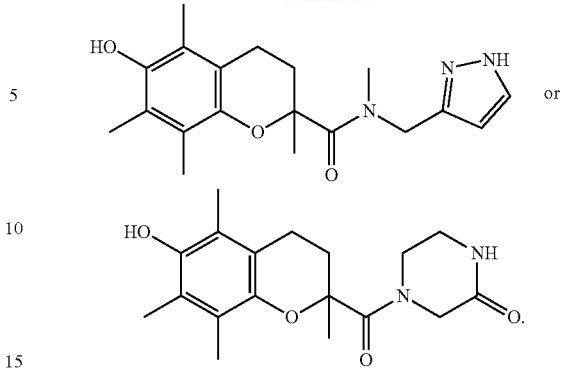

In embodiments of the pharmaceutical compositions, the compound, or pharmaceutically acceptable salt thereof, is included in a therapeutically effective amount.

The pharmaceutical composition may be prepared and administered in a wide variety of dosage formulations. Compounds described may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Therapeutically effective amounts for use in humans may be determined from animal models. For example, a dose for humans can be formulated to achieve a concentration that has been found to be effective in animals. The dosage in humans can be adjusted by monitoring response of the constipation or dry eye to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch.1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethyleneblock polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

III. Methods

Provided herein is a method of treating or preventing loss of RPE cells or function (e.g., loss associated with AMD) in a subject. In one aspect, the method includes administering to the subject an effective amount of the compound (e.g. formulae (I) or (II) described above (including all embodiments thereof) and a pharmaceutically acceptable salts. Subject to be treated are identified using methods know in the art, e.g., those described in Sacconi et al., 2017, Ophthalmol Ther. 6(1): 69-77 and P. T. V. M. de Jong; N Engl J Med 2006; 355:1474-1485, hereby incorporated by reference.

In embodiments, the subject has AMD. In embodiments, the AMD is dry AMD. In embodiments, the AMD is wet AMD. In embodiments, the subject has GA. In embodiments, the AMD comprises RPE degeneration (such as death) or GA. In embodiments, the compound is administered by ocular administration (e.g., topical, intravitreal, intracameral, subconjunctival, subtendon, retrobulbar, or posterior juxtascleral administration). In embodiments, the compound is administered by intraocular injection. In embodiments, the compound is administered topically.

In embodiments, an effective amount is an amount that treats (e.g., reduces) the loss of RPEs function (e.g., by RPE death or degeneration) in the eye of a subject. In embodiments, an effective amount is an amount that treats AMD or a symptom thereof in a subject. In embodiments, an effective amount is an amount that treats GA or a symptom thereof in a subject. In embodiments, an effective amount is an amount that reduces the accumulation or amount of ox-LDL in ocular cells, such as RPEs, of a subject (e.g., in the lysosomes of RPEs). In embodiments, an effective amount is an amount that reduces the crystallization of ox-LDL in ocular cells (e.g., RPEs) of a subject. In certain embodiments, an effective amount is an amount that reduces lysosomal destabilization in ocular cells (e.g., RPEs) of a subject. In embodiments, an effective amount is an amount that reduces activation of an inflammasome (such as an NLRP3-inflammasome) in ocular cells (e.g., RPEs) of a subject. In embodiments, an effective amount is an amount that reduces the expression, secretion, or level (e.g., amount of protein) of a pro-inflammatory cytokine such as interleukin-1beta (IL-1β) or I-18 in ocular cells (such as RPEs) or tissue (e.g., in the retina or vitreous) of a subject. In embodiments, an effective amount is an amount that reduces the level of at least 1, 2, 3, 4, or 5 reactive oxygen species (ROS) in ocular cells (such as RPEs) or tissue (e.g., in the retina or vitreous) of a subject. In embodiments, an effective amount is an amount that reduces ox-LDL-induced ROS formation in RPEs of a subject. Non-limiting examples of ROS include peroxides (e.g., $H_2O_2$), superoxide ($\bullet O^{-2}$), hydroxyl radicals (e.g., $\bullet OH$), and singlet oxygen ($^1O_2$).

IV. Non-Limiting Embodiments

Embodiment 1

A method of treating or preventing age-related macular degeneration in a subject, the method comprising administering to the subject an effective amount of a compound having a formula (I),

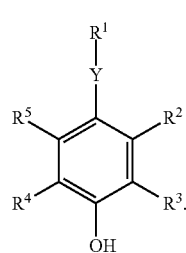

Y, R, $R^2$, $R^3$, $R^4$, $R^5$ and $R^6$ are as described herein.

Embodiment 2

The method of Embodiment 1, wherein Y is —NH—.

Embodiment 3

The method of Embodiment 2, wherein $R^1$ is —C(O)$R^{1C}$ and $R^{1C}$ is unsubstituted $C_1$-$C_4$ alkyl.

Embodiment 4

The method of Embodiment 1, wherein Y is —O—.

Embodiment 5

The method of Embodiment 4, wherein $R^1$ is hydrogen, or substituted or unsubstituted $C_1$-$C_4$ alkyl.

Embodiment 6

The method of any one of Embodiments 1-5, wherein $R^2$ and $R^5$ are independently hydrogen or unsubstituted $C_1$-$C_4$ alkyl.

Embodiment 7

The method of any one of Embodiments 1-6, wherein $R^3$ and $R^4$ are independently hydrogen, or substituted or unsubstituted $C_1$-$C_4$ alkyl.

Embodiment 8

The method of Embodiment 1, wherein the compound has a formula (II),

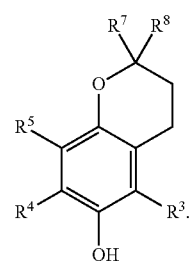

$R^3$, $R^4$, $R^5$, $R^7$ and $R^8$ are as described herein.

Embodiment 9

The method of Embodiment 8, wherein $R^7$ is hydrogen, or unsubstituted $C_1$-$C_4$ alkyl.

Embodiment 10

The method of Embodiment 9, wherein $R^7$ is —$CH_3$.

Embodiment 11

The method of anyone of Embodiments 8-10, wherein $R^8$ is represented as:

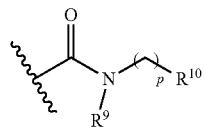

p, $R^9$ and $R^{10}$ are as described herein.

Embodiment 12

The method of Embodiment 11, wherein $R^9$ is hydrogen or unsubstituted $C_1$-$C_4$ alkyl.

Embodiment 13

The method of any one of Embodiments 11-12, wherein $R^{10}$ is

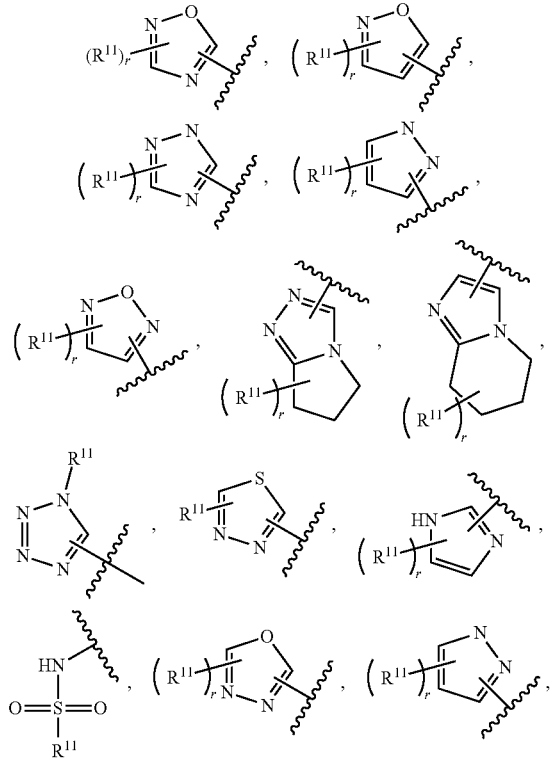

r and $R^{11}$ are as described herein.

Embodiment 14

The method of Embodiment 13, wherein $R^{11}$ is hydrogen or unsubstituted $C_1$-$C_4$ alkyl.

Embodiment 15

The method of anyone of Embodiments 8-11, wherein $R^9$ and $R^{10}$ together with the nitrogen attached thereto are joined to form:

q and $R^{12}$ are as described herein.

Embodiment 16
The method of Embodiment 15, wherein $R^{12}$ is hydrogen, unsubstituted $C_1$-$C_4$ alkyl, —OH, —OCH$_3$, —CH$_2$OH or —CH$_2$CH$_2$OH.
Embodiment 17
The method of anyone of Embodiments 1-16, wherein the compound is:
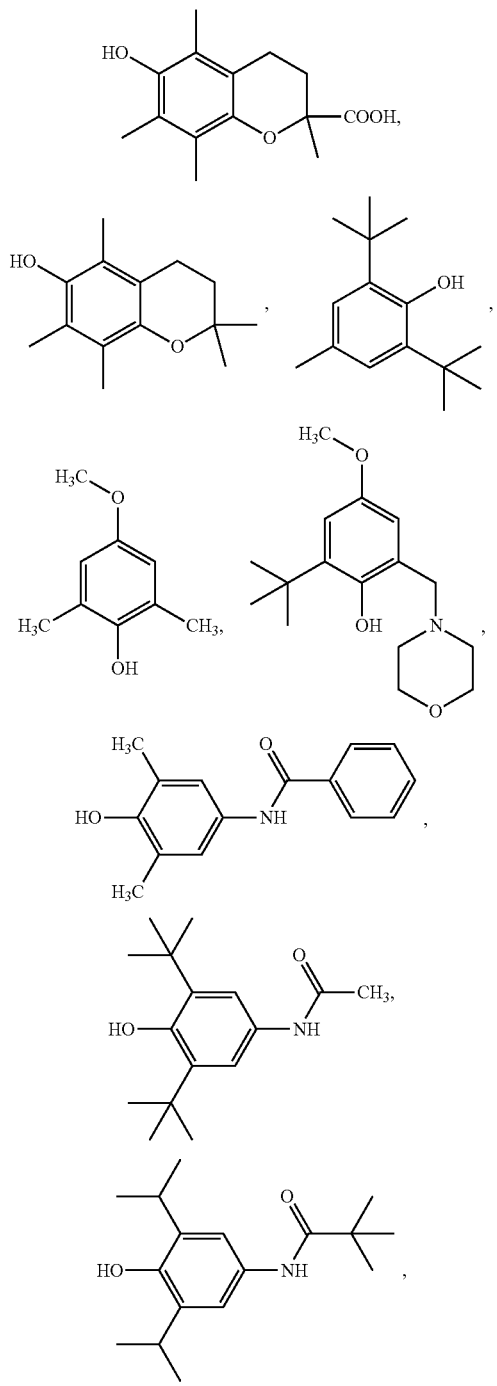
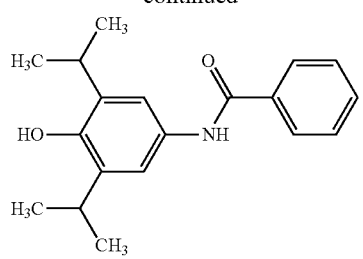
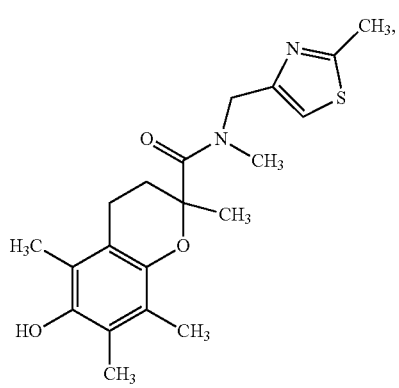
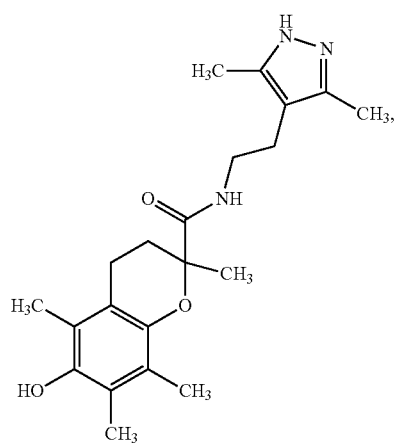
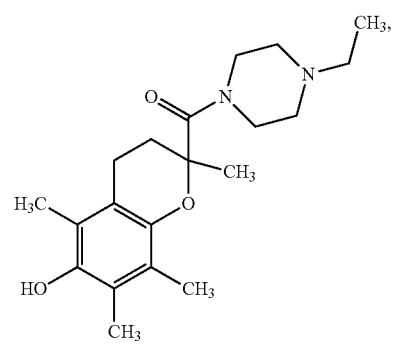
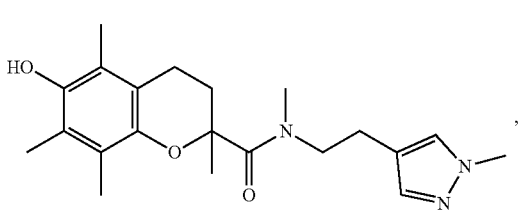

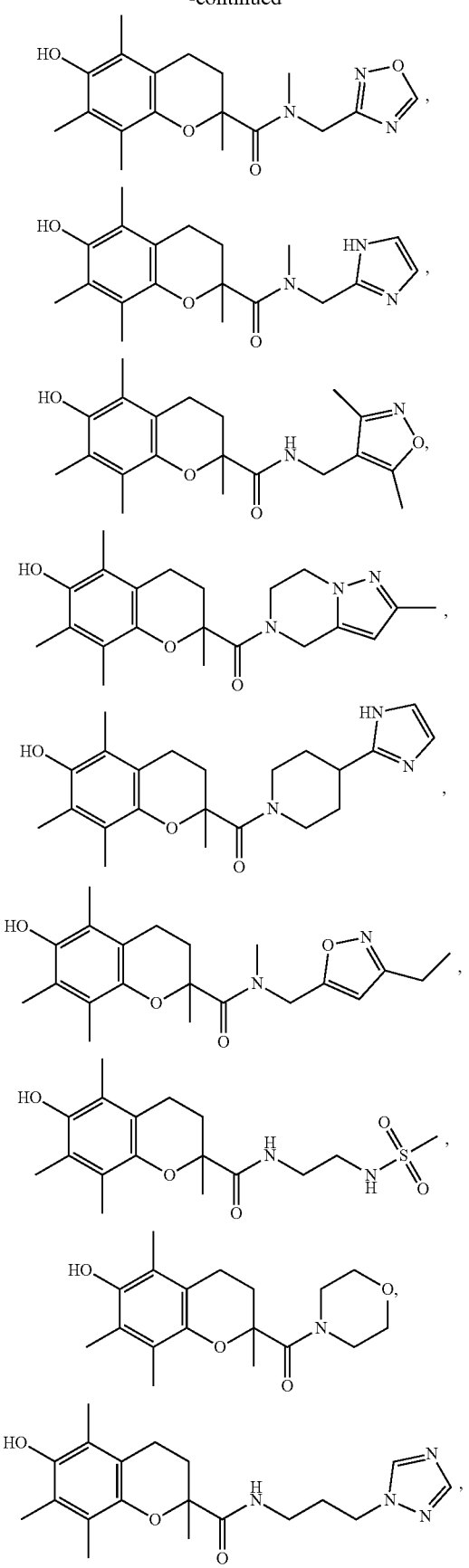
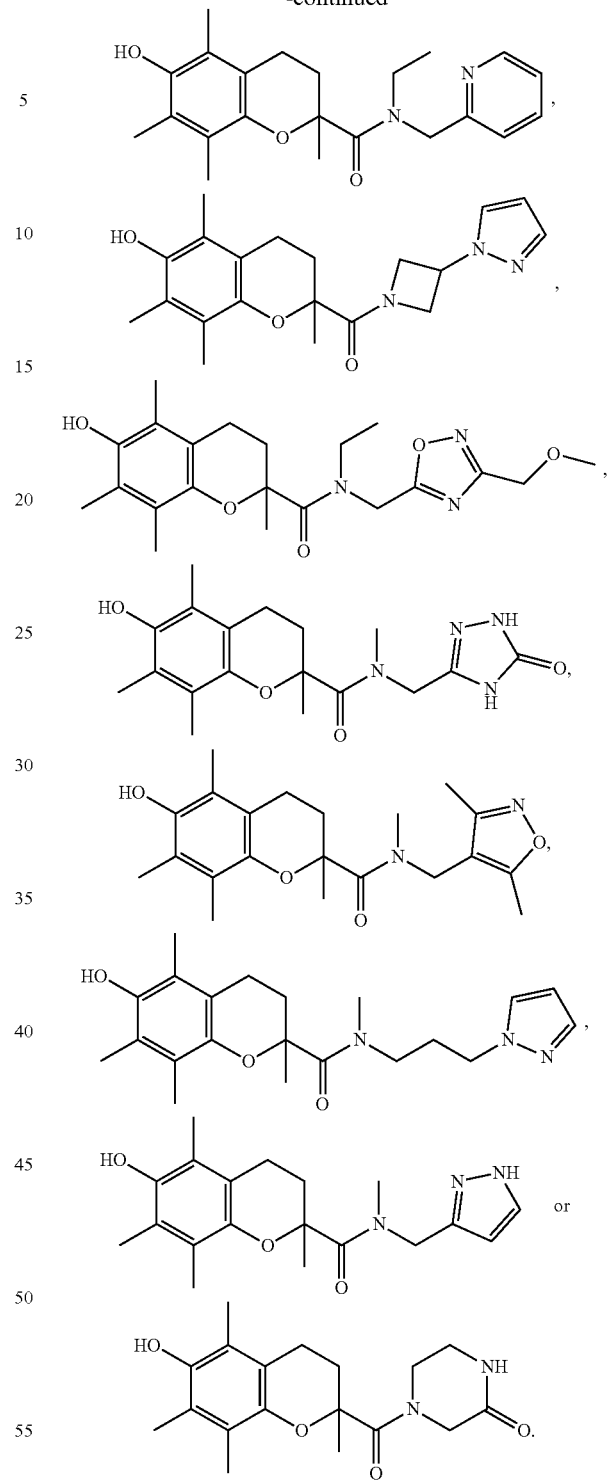
The method of any one of Embodiments 1-17, wherein the age-related macular degeneration comprises retinal pigment epithelium (RPE) degeneration or geography atrophy (GA).
Embodiment 19
The method of any one of Embodiments 1-18, wherein the compound is administered by intraocular injection.

Embodiment 20

The method of any one of Embodiments 1-18, wherein the compound is administered topically.

Embodiment 21

A pharmaceutical composition comprising a formula (I),

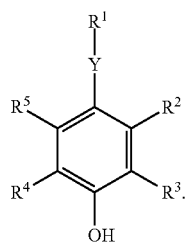

(I)

Y, $R^1$, $R^2$, $R^3$, $R^4$, $R^5$ and $R^6$ are as described herein.

Embodiment 22

The pharmaceutical composition of Embodiment 21, wherein Y is —NH—.

Embodiment 23

The pharmaceutical composition of Embodiment 22, wherein $R^1$ is —C(O)$R^{1C}$ and $R^{1C}$ is unsubstituted $C_1$-$C_4$ alkyl.

Embodiment 24

The pharmaceutical composition of Embodiment 21, wherein Y is —O—.

Embodiment 25

The pharmaceutical composition of Embodiment 24, wherein $R^1$ is hydrogen, or substituted or unsubstituted $C_1$-$C_4$ alkyl.

Embodiment 26

The pharmaceutical composition of any one of Embodiments 21-25, wherein $R^2$ and $R^5$ are hydrogen, or substituted or unsubstituted $C_1$-$C_4$ alkyl.

Embodiment 27

The pharmaceutical composition of any one of Embodiments 21-26, wherein $R^2$ and $R^5$ are independently unsubstituted $C_1$-$C_4$ alkyl.

Embodiment 28

The pharmaceutical composition of any one of Embodiments 21-27, wherein $R^3$ and $R^4$ are independently hydrogen, or substituted or unsubstituted $C_1$-$C_4$ alkyl.

Embodiment 29

The pharmaceutical composition of Embodiment 21, wherein the compound has a formula (II),

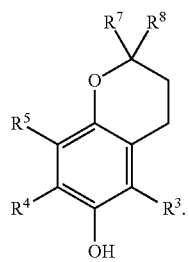

(II)

$R^3$, $R^4$, $R^5$, $R^7$ and $R^8$ are as described herein.

Embodiment 30

The pharmaceutical composition of Embodiment 29, wherein $R^7$ is hydrogen, or unsubstituted $C_1$-$C_4$ alkyl.

Embodiment 31

The pharmaceutical composition of any one of Embodiments 29-30, wherein $R^7$ is —$CH_3$.

Embodiment 32

The pharmaceutical composition of any one of Embodiments 29-31, wherein $R^8$ is represented as

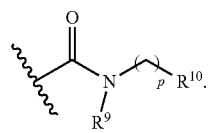

p, $R^9$ and $R^{10}$ are as described herein.

Embodiment 33

The pharmaceutical composition of Embodiment 32, wherein $R^9$ is hydrogen or unsubstituted $C_1$-$C_4$ alkyl.

Embodiment 34

The pharmaceutical composition of any one of Embodiments 32-33, wherein $R^{10}$ is

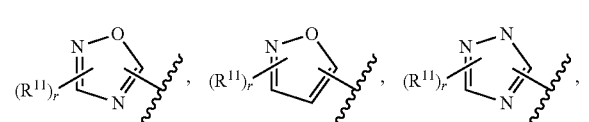

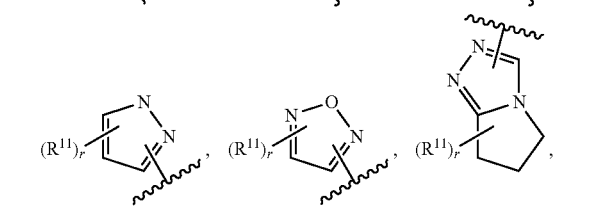

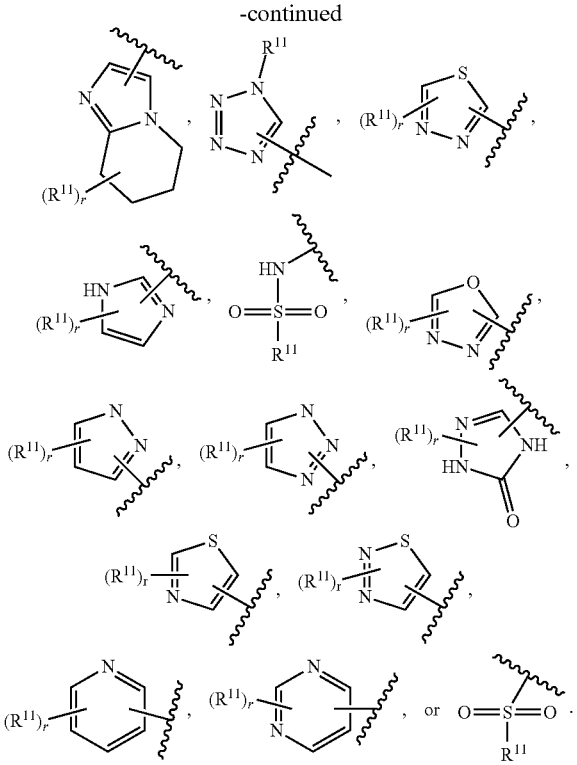

$R^{11}$ and r are as described herein.

Embodiment 35

The pharmaceutical composition of Embodiment 34, wherein $R^{11}$ is hydrogen, unsubstituted $C_1$-$C_4$ alkyl.

Embodiment 36

The pharmaceutical composition of any one of Embodiments 29-32, wherein $R^9$ and $R^{10}$ together with the nitrogen attached thereto are joined to form:

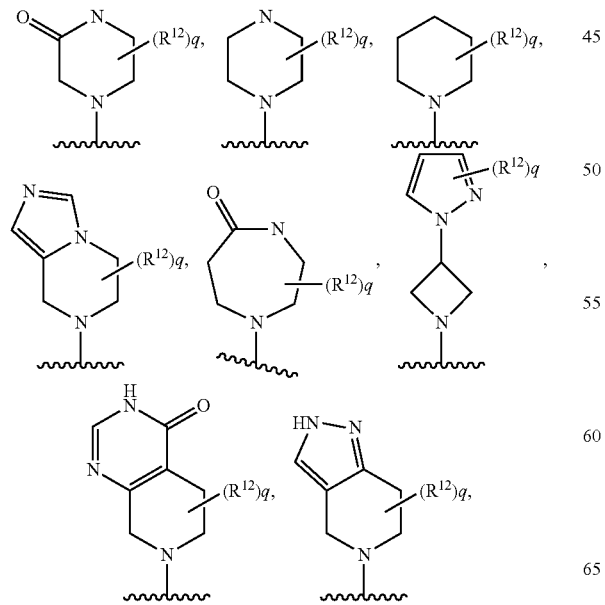

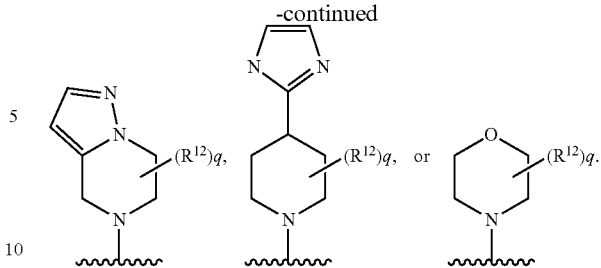

$R^{12}$ and q are as described herein.

Embodiment 37

The pharmaceutical composition of Embodiment 36, wherein $R^{12}$ is hydrogen, unsubstituted $C_1$-$C_4$ alkyl, —OH, —OCH$_3$, —CH$_2$OH or —CH$_2$CH$_2$OH.

Embodiment 38

The pharmaceutical composition of any one of Embodiments 21-37, wherein the compound is:

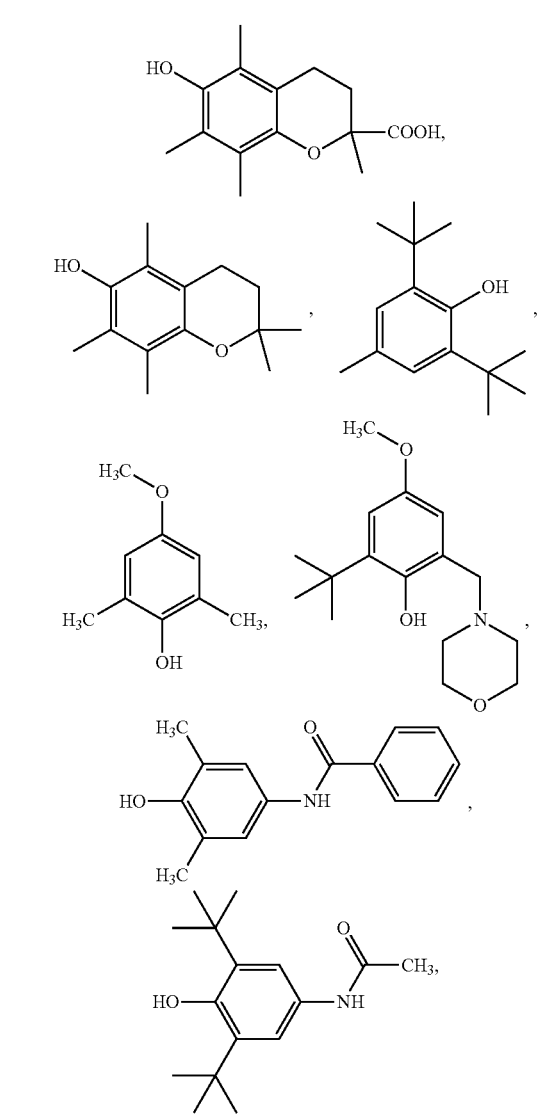

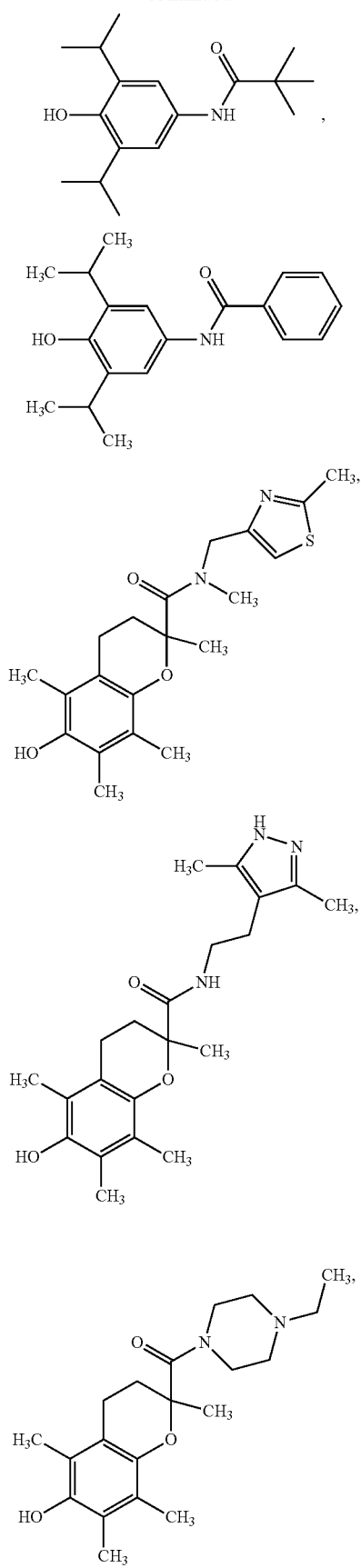
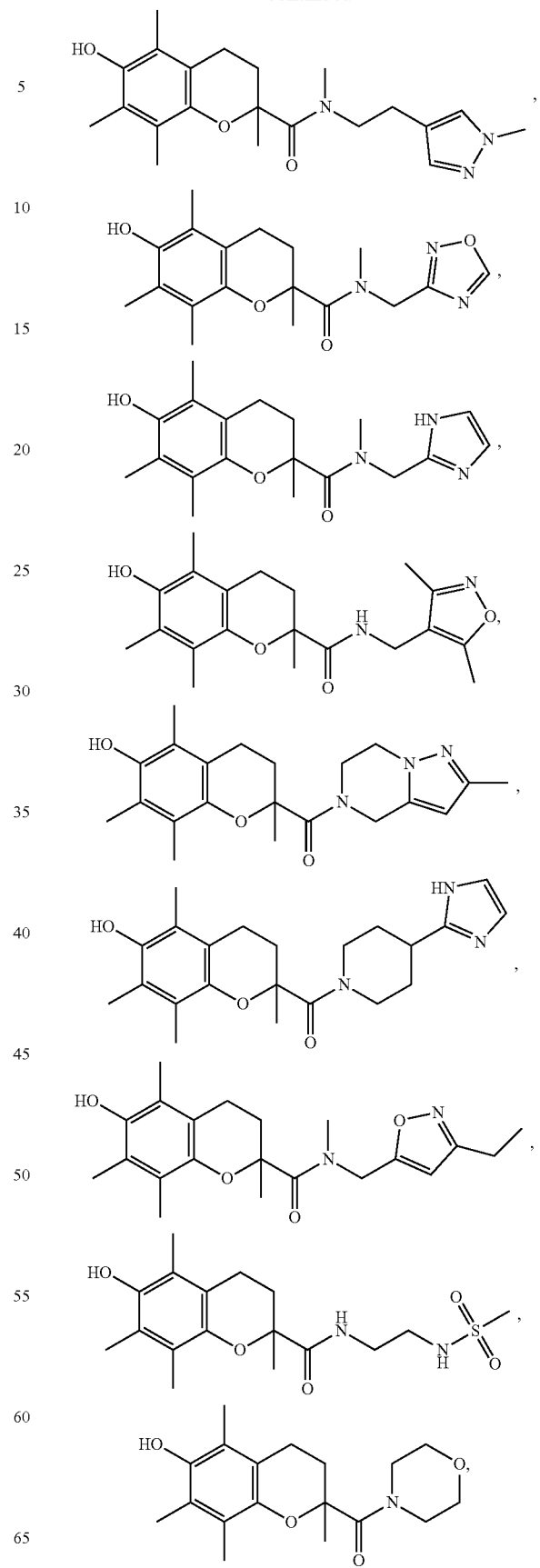

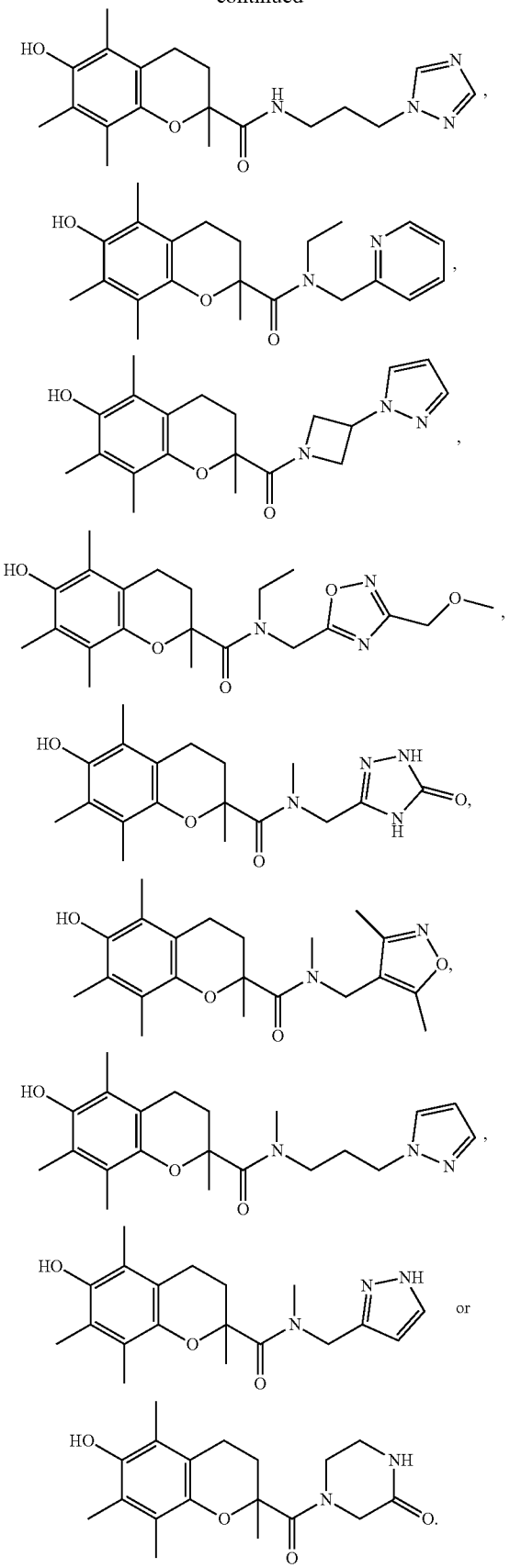

Embodiment 39

The pharmaceutical composition of any one of Embodiments 21-38, further comprising an ophthalmologically acceptable vehicle.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1. Hindered Phenol-Containing Compounds for Inhibiting RPE Degeneration or GA Associated with AMD There is no established treatment for dry AMD, and methods to protect the RPE from degeneration is a promising area of focus. Although the exact mechanisms underlying the pathogenesis of AMD remain unknown, accumulation of oxidized lipid-containing drusen beneath the RPE has been strongly associated with AMD pathogenesis. For example, oxidized lipid-containing drusen are the first sign of AMD (Wang, L., et al., PLoS One, 2010. 5(4): p. e10329), hypercholesterolemia is a risk factor for the disease (van Leeuwen, R., et al., Eur J Epidemiol, 2003. 18(9): p. 845-54) and cholesterol-lowering statins may provide some benefit in individuals aged 68 and older (Barbosa, D. T., et al., Eye (Lond), 2014. 28(4): p. 472-80), suggesting a role for dysfunctional lipid metabolism in promoting drusen formation dry AMD.

The RPE plays a key role in lipid homeostasis in the retina. RPE cells express a variety of receptors that mediate the uptake of lipids including oxidized low-density lipoproteins (ox-LDL). Apically delivered lipids, including photo-oxidized photoreceptor outer segments (Sun, M., et al., J Biol Chem, 2006. 281(7): p. 4222-30), are normally "cleared" by the RPE to the underlying choroid (Ishida, B. Y., et al., Br J Ophthalmol, 2006. 90(5): p. 616-20). The mechanism of lipid deposition in AMD is poorly understood, but clinical and experimental observations have shown accumulation of ox-LDL and phospholipids in RPE cells in AMD (reviewed in Curcio, C. A., et al., Br J Ophthalmol, 2011. 95(12): p. 1638-45; Curcio, C. A., et al., Invest Ophthalmol Vis Sci, 2001. 42(1): p. 265-74). This can have important consequences for cellular function, as uptake of oxidized lipids by RPE cells decreases lysosomal protease function (Krohne, T. U., et al., Exp Eye Res, 2010. 90(2): p. 261-6). Given that lysosomal function in RPE cells decreases with age (Chen, H., et al., Invest Ophthalmol Vis Sci, 2009. 50(4): p. 1895-902; Jason Lim, et al., *Invest Ophthalmol Vis Sci* 2014), lysosomal accumulation of oxidized lipids could be particularly pronounced in elderly individuals.

Lysosomal accumulation of ox-LDL can have profound impacts on cellular health. In macrophages, accumulation of ox-LDL in the lysosomes leads to crystallization of ox-LDL, which causes lysosomal destabilization, activation of the nucleotide-binding domain, leucine-rich-containing family, pyrin domain-containing-3 (NLRP3)-inflammasome, release of interleukin-1beta (IL-10) and IL-18, and ultimately cell death (Sheedy, F. J., et al., Nat Immunol, 2013. 14(8): p. 812-20). Similar effects were observed in primary human RPE and in ARPE-19 cells, in that they accumulate ox-LDL in the lysosomes. ARPE-19 cells exposed to ox-LDL (but not to native LDL) released pro-inflammatory cytokines at higher levels, expressed higher levels of NLRP3-inflammasome activation markers and cell death, and similar results were obtained from primary human RPE (Gnanaguru, G., et al., Invest Ophthalmol Vis Sci, 2016. 57(11): p. 4704-12). Given that inflammasome activation has also been observed in the RPE cells of human eyes with AMD, these effects are particularly interesting (Tseng, W. A., et al., Invest Ophthalmol Vis Sci, 2013. 54(1): p. 110-20).

Taken together, these data support a role for an ox-LDL-lysosome-inflammasome pathway in the pathogenesis of GA. However, the detailed mechanism of lysosomal accumulation of ox-LDL, inflammasome activation, and RPE death has not been clearly defined. Because ox-LDL uptake by vascular endothelial cells can induce formation of cytotoxic reactive oxygen species (ROS), which contributes to vascular damage associated with pathogenesis of atherosclerosis (Ding, Z., et al., Sci Rep, 2013. 3: p. 1077), we investigated the formation of ROS upon ox-LDL treatment in RPE. We confirmed that ox-LDL potently induce ROS in RPE cells (FIG. 1), which can contribute directly and/or indirectly to the activation of the inflammasome pathway and RPE death in AMD (Abais, J. M., et al., Antioxid Redox Signal, 2015. 22(13): p. 1111-29; Shaw, P. X., et al., AIMS Mol Sci, 2016. 3(2): p. 196-221).

In terms of translational research, while blocking the ox-LDL-inflammasome pathway would seem like a viable approach, antagonism of this pathway would be therapeutically problematic, as specifically inhibiting selected component(s) of these pathways would be expected to have off target effects on other important cellular functions. For example, the lipid scavenger receptor CD36 plays important roles in both lipid uptake and phagocytosis of photoreceptor outer segments (Sun, M., et al., J Biol Chem, 2006. 281(7): p. 4222-30), and the inflammasome complex is a common internal sensor for various intracellular signals that modulate inflammation and cellular homeostasis (Petrilli, V., et al., Curr Opin Immunol, 2007. 19(6): p. 615-22; Doyle, S. L., et al., Nat Med, 2012. 18(5): p. 791-8). Since young and healthy RPE cells can effectively process ox-LDL without inducing inflammasome activation (Barbosa, D. T., et al., Eye (Lond), 2014. 28(4): p. 472-80; Jason Lim, W. L., Alan M Laties and Claire H Mitchell, in *Invest Ophthalmol Vis Sci* 2014), a potential therapeutic approach would be to suppress the cytotoxic effects of oxidized lipid upon lysosomal accumulation, and thereby prevent the activation of the inflammasome pathway and RPE degeneration in dry AMD.

Figure 2:
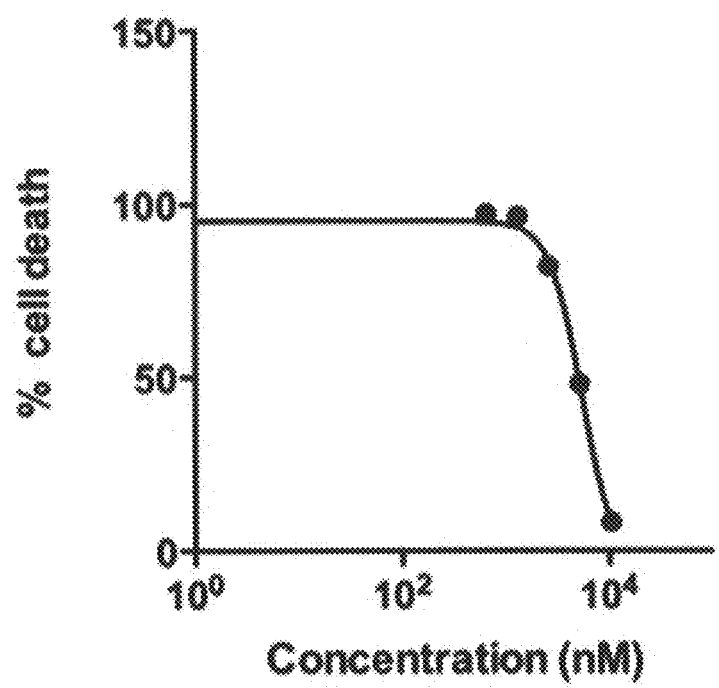
FIG. 2 is a graph showing dose-dependent inhibition of ox-LDL-induced RPE death by trolox. ARPE-19 cells were treated with 200 µg/ml of ox-LDL for 48 hours with and without different concentrations of trolox (from 0.65 µM to 10.4 µM). Cell death was measured by lactate dehydrogenase (LDH) release assay (CytoTox96® Non-Radioactive Cytotoxicity Assay, Promega, Madison, Wis.). Data=mean±standard error of the mean (SEM), non-linear regression (GraphPad Prism 6).
Figure 3:
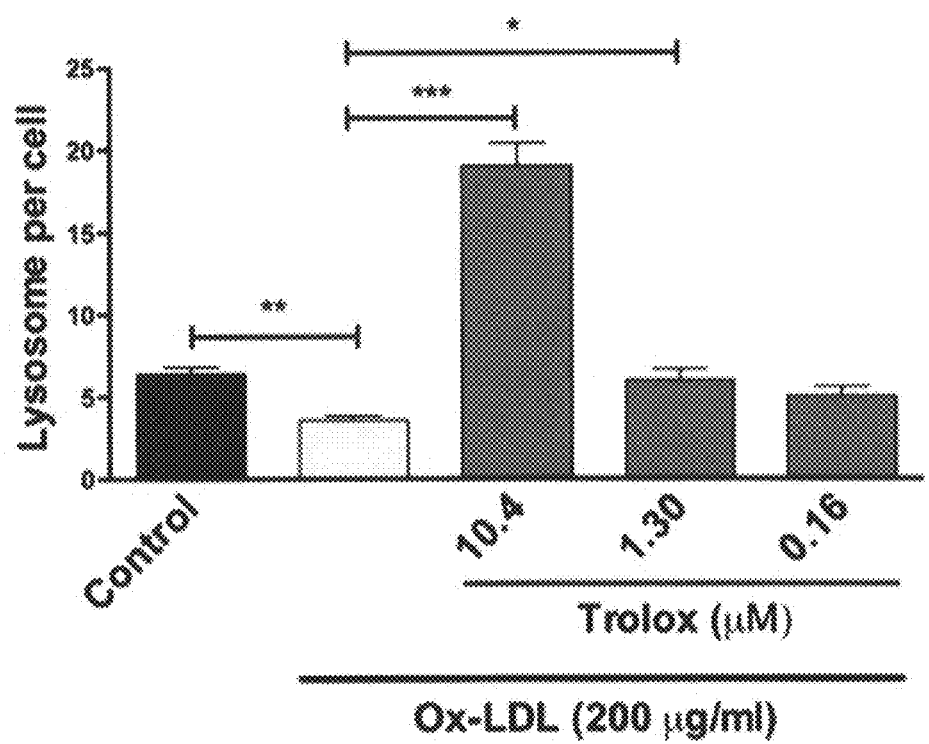
FIG. 3 is a graph showing that trolox dose-dependently suppresses ox-LDL-induced lysosomal destabilization in RPE. ARPE-19 cells were treated with ox-LDL with and without different concentrations of trolox for 36 hours. Lysosomal integrity was determined by LysoTracker staining (ThermoFisher Scientific), followed by image analysis to quantify the number of intact lysosomes per cell. Ox-LDL significantly reduced the number of intact lysosomes per cell, and trolox at 10.4 µM induced higher number of intact lysosomes per cell compared to control in the presence of ox-LDL. Data=mean±SEM, *$P<0.05$, $P<0.01$, *$P<0.001$ compared to ox-LDL group, analysis of variance (ANOVA).
Figure 4:
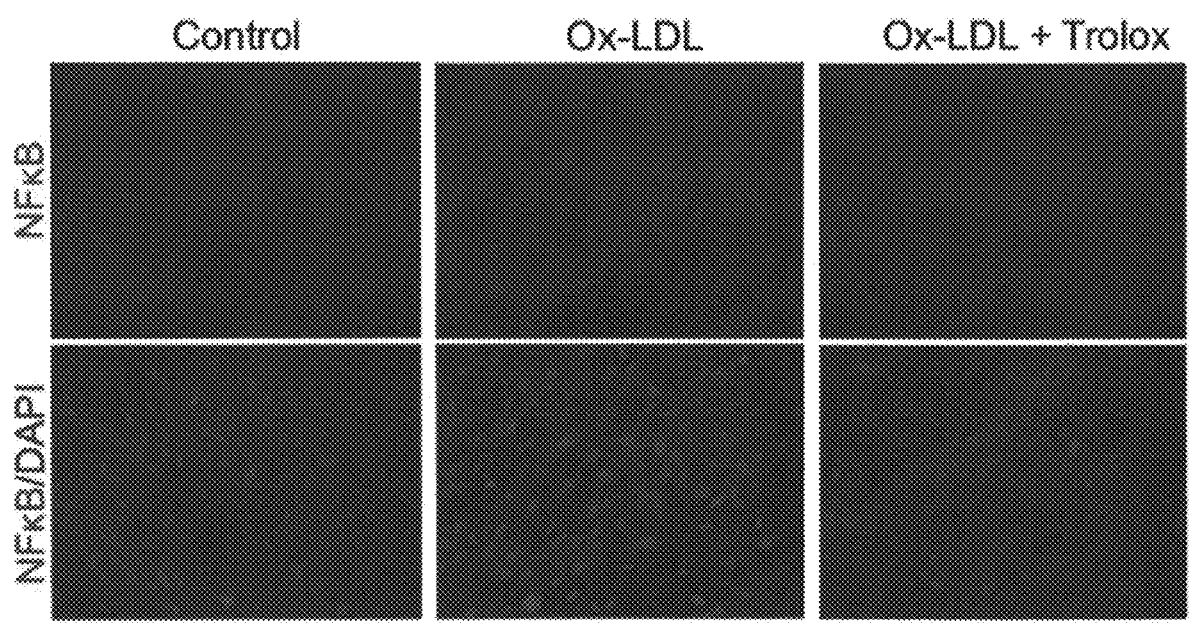
FIG. 4 shows that trolox suppresses NF-κB activation induced by ox-LDL in RPE. ARPE-19 cells were treated with 200 µg/ml ox-LDL with and without trolox (10.4 µM) for 36 hours, activation of nuclear factor kappa-light-chain-enhancer of activated B cells (NF-κB) can be readily detected in ox-LDL treated cells, and trolox suppressed NF-κB activation.
Figure 5A:
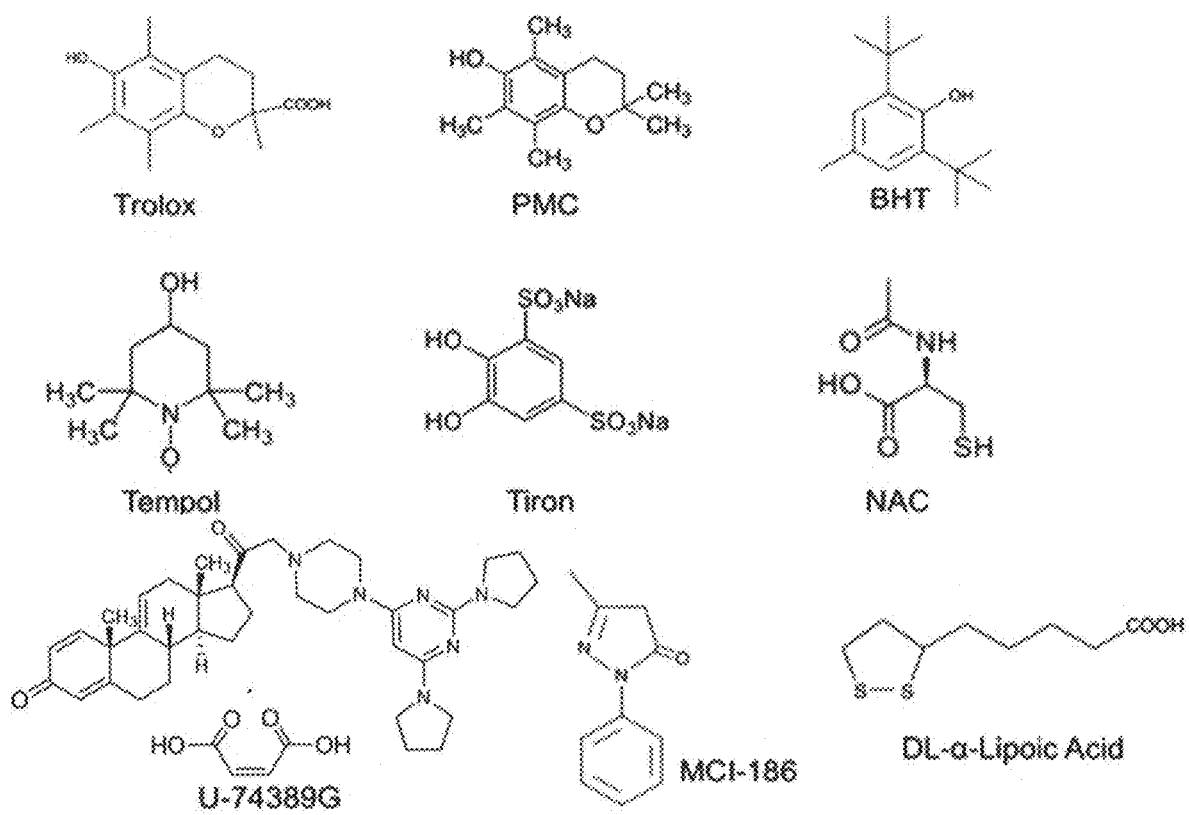
FIG. 5A shows the structures of the various anti-oxidants tested.
Figure 5B:
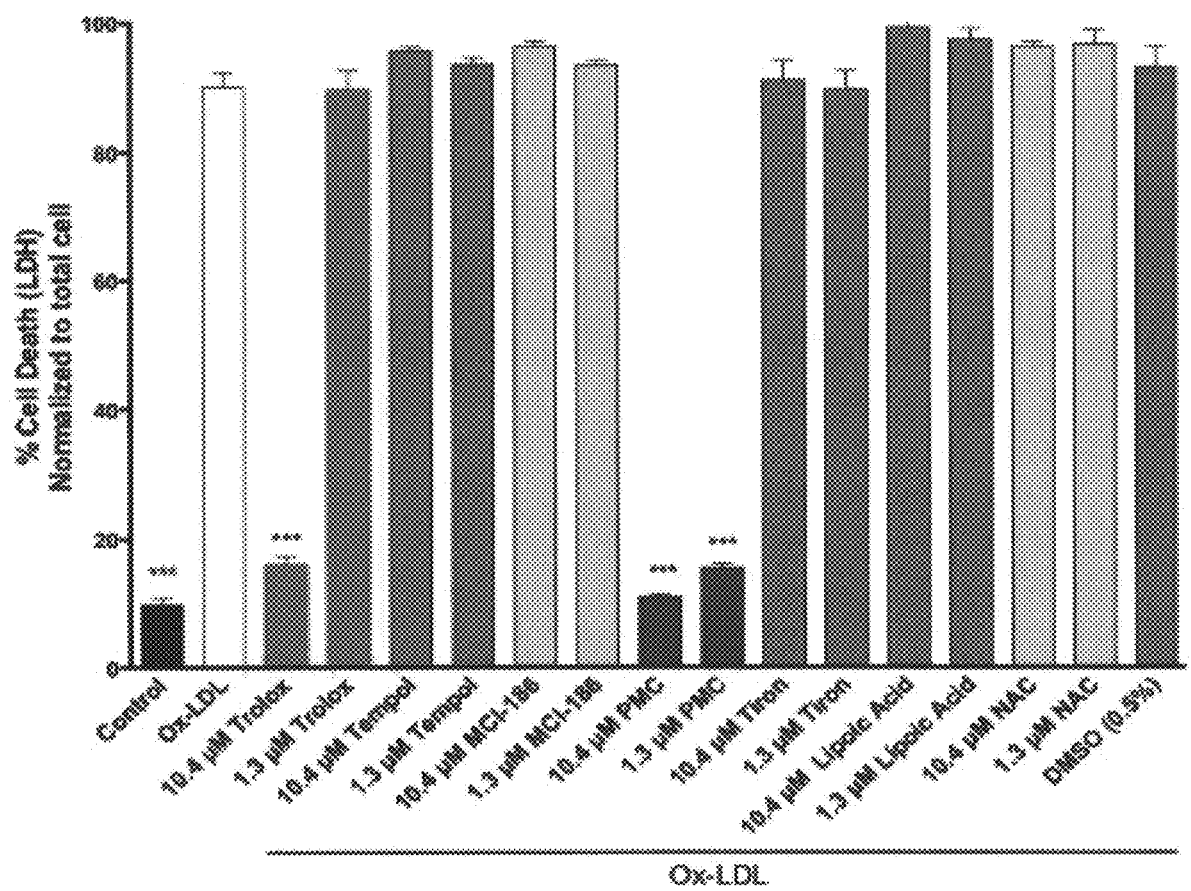
FIGS. 5B and 5C are graphs showing RPE protection by selective anti-oxidants with a hindered phenol group. ARPE-19 cells were treated with ox-LDL (200 µg/ml) with and without different concentrations of various anti-oxidants. Cell death was measured by LDH release assay. Data=mean±SEM, *$P<0.05$, ***$P<0.001$ compared to ox-LDL group, ANOVA.
Figure 5C:
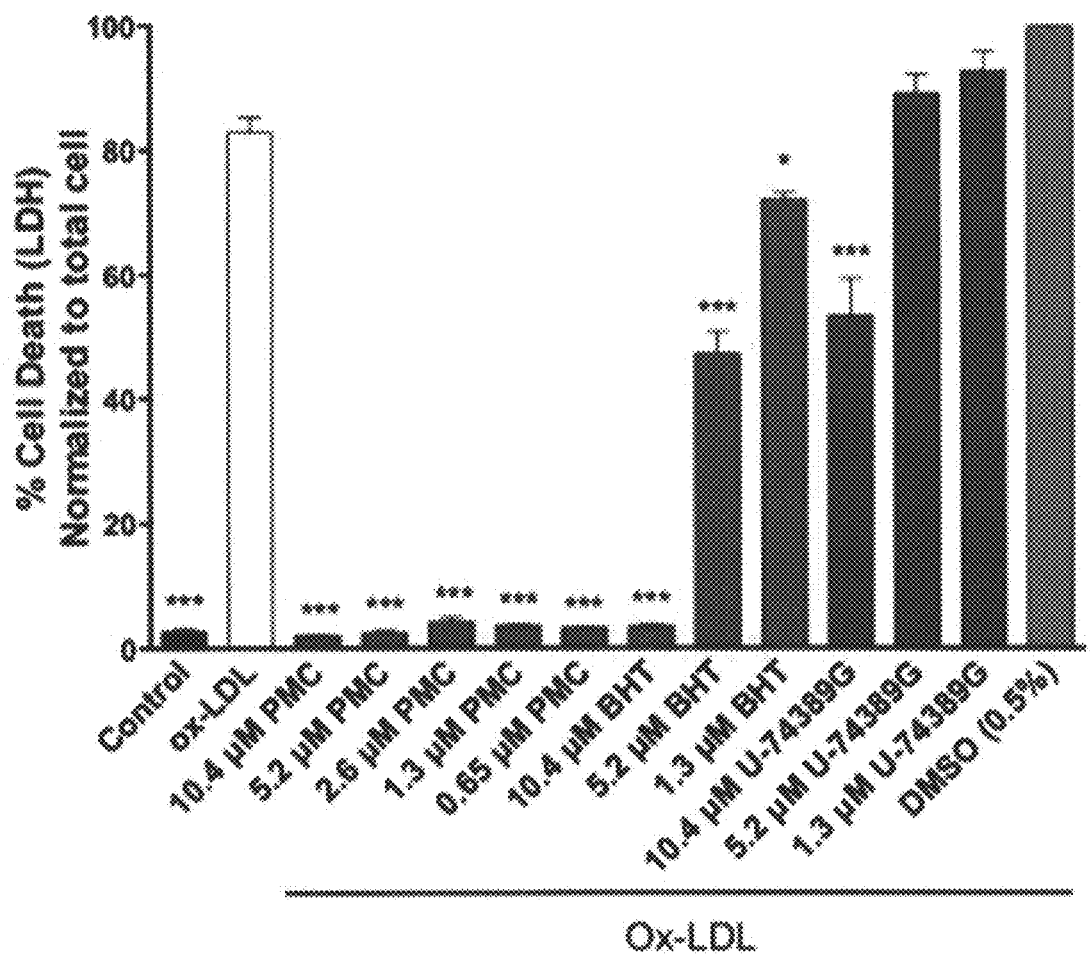

In order to identify drugs to suppress RPE degeneration in AMD, the ox-LDL-induced inflammasome activation and RPE death were used as a model system for the screening; ox-LDL uptake by RPE likely plays a role in AMD pathogenesis. Testing different anti-oxidants was focused on because of the observed ox-LDL-induced ROS formation in RPE. From this screening, the antioxidant trolox (6-hydroxy-2,5,7,8-tetramethylchroman-2-carboxylic acid) dose-dependently suppressed ox-LDL-induced RPE death, with an estimated EC50 of about 5.4 µM (FIG. 2). Further experiments showed that trolox also preserved lysosomal integrity (FIG. 3), suppressed pro-inflammatory transcription factor NF-κB activation and suppressed ROS formation in RPE cells upon ox-LDL treatment (FIGS. 1 and 4). In order to understand the mechanism of trolox-mediated protection and to identify more potent compounds for protecting RPE against ox-LDL, different classes of anti-oxidants were tested in this assay, and it was discovered that most of the compounds containing a "hindered phenol" group were effective in protecting RPE. For example hindered phenol-containing trolox and PMC (2,2,5,7,8-pentamethyl-6-chromanol) are significantly more effective than the anti-oxidants tempol, tiron, N-acetyl-L-cysteine, MCI-186 (edaravone), DL-α-lipoic acid (thioctic acid) and U-74389G, which although they are potent anti-oxidants in other assays, lack a hindered phenol group (Dodd, S., et al., Expert Opin Biol Ther, 2008. 8(12): p. 1955-62; Kikuchi, K., et al., J Pharmacol Exp Ther, 2009. 329(3): p. 865-74; Ledenev, A. N., et al., Biochem Int, 1986. 13(2): p. 391-6; Vorobjeva, N. V. and B. V. Pinegin, Immunobiology, 2016. 221(2): p. 208-19; Biewenga, G. P., G. R. Haenen, and A. Bast, Gen Pharmacol, 1997. 29(3): p. 315-31; Ishizaki, N., et al., Transplant Proc, 1997. 29(1-2): p. 1333-4; Babich, H., Environ Res, 1982. 29(1): p. 1-29; Cos, P., et al., J Pharm Pharmacol, 2003. 55(9): p. 1291-7) (FIG. 5).

Figure 6:
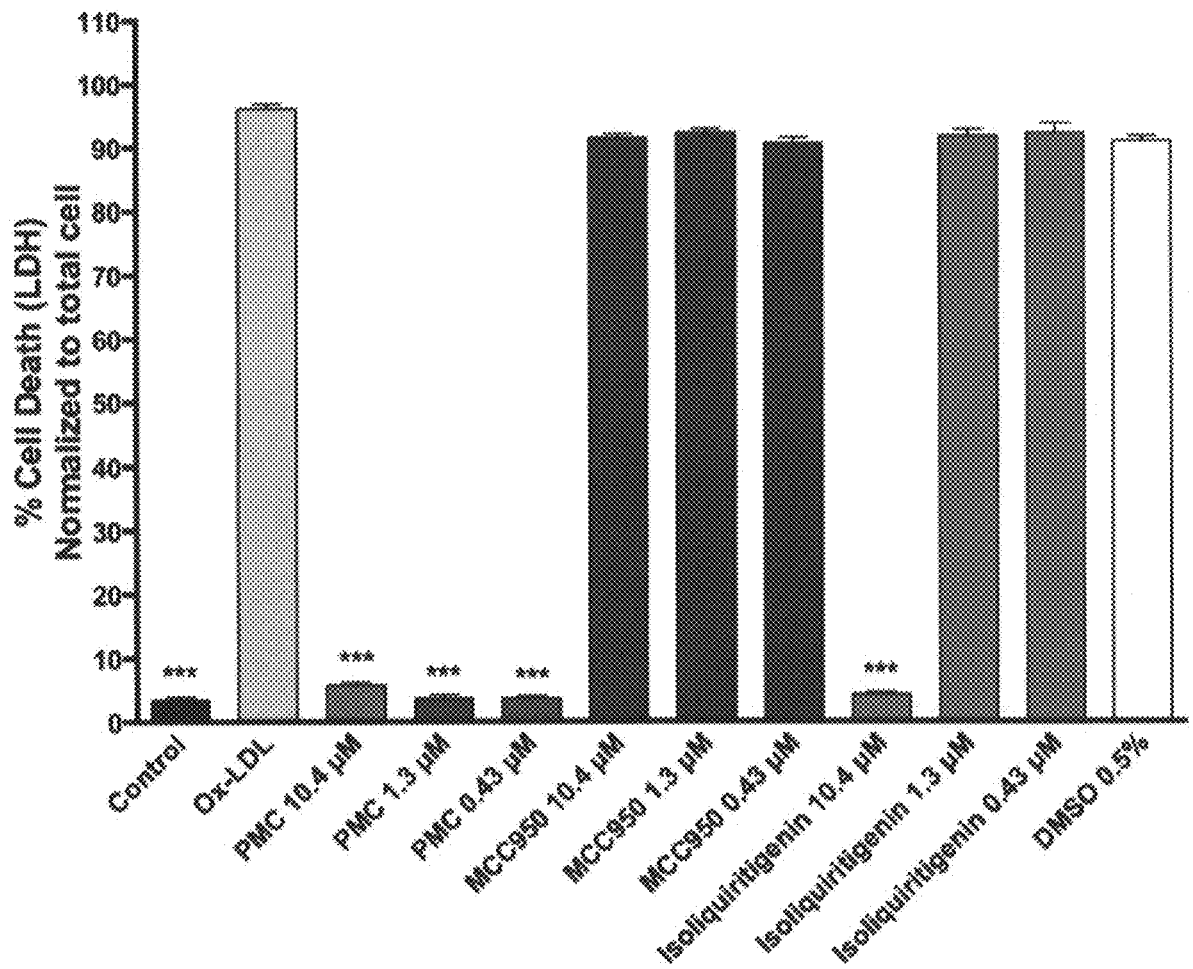
FIG. 6 is a graph comparing RPE protection activity of hindered phenol-containing 2,2,5,7,8-pentamethyl-6-chromanol (PMC) and selective inhibitors of nucleotide-binding domain, leucine-rich-containing family, pyrin domain-containing-3 (NLRP3) inflammasome activation. ARPE-19 cells were treated with ox-LDL (200 µg/ml) with and without different concentrations of PMC and selective inhibitors of NLRP3 inflammasome activation, MCC950 and isoliquiritigenin. Cell death was measured by LDH release assay. Data=mean±SEM, ***$P<0.001$ compared to ox-LDL group, ANOVA.

Because activation of the NLRP3 inflammasome and caspase-1 pathway plays an important role in ox-LDL-induced RPE death, the RPE protective effects of PMC were also compared with known inhibitors of inflammasome activation which are actively being developed for treating inflammatory neurodegenerative diseases (Guo, H., J. B. Callaway, and J. P. Ting, Nat Med, 2015. 21(7): p. 677-87). While PMC is very potent in protecting ox-LDL-induced RPE cell death (>95% protection at 0.43 µM), the highly selective NLRP3 inflammasome activation inhibitor MCC950 (Coll, R. C., et al., Nat Med, 2015. 21(3): p. 248-55) ($IC_{50}$ 7.5 nM) did not have any protective effect even at high dose (10.4 µM) and isoliquiritigenin (Honda, H., et al., J Leukoc Biol, 2014. 96(6): p. 1087-100), another potent inhibitor of NLRP3 inflammasome activation only protected RPE cells at high dose (10.4 µM) (FIG. 6). These data demonstrate hindered phenol containing compounds are superior in protecting ox-LDL-induced RPE cell death when compare to drugs that selectively inhibit NLRP3 inflammasome activation.

Figure 7A:
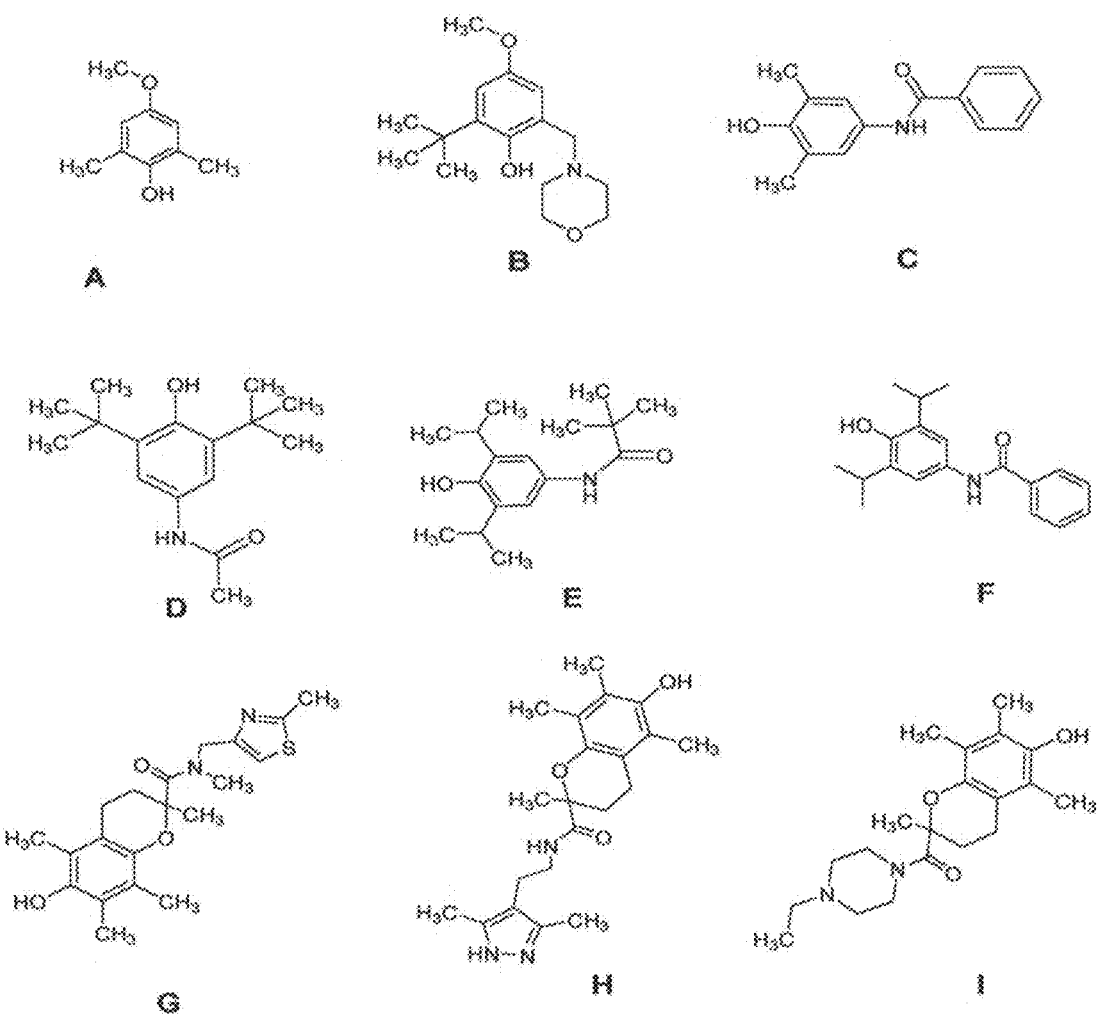
FIG. 7A shows structures of the different experimental analogs tested.
Figure 7B:
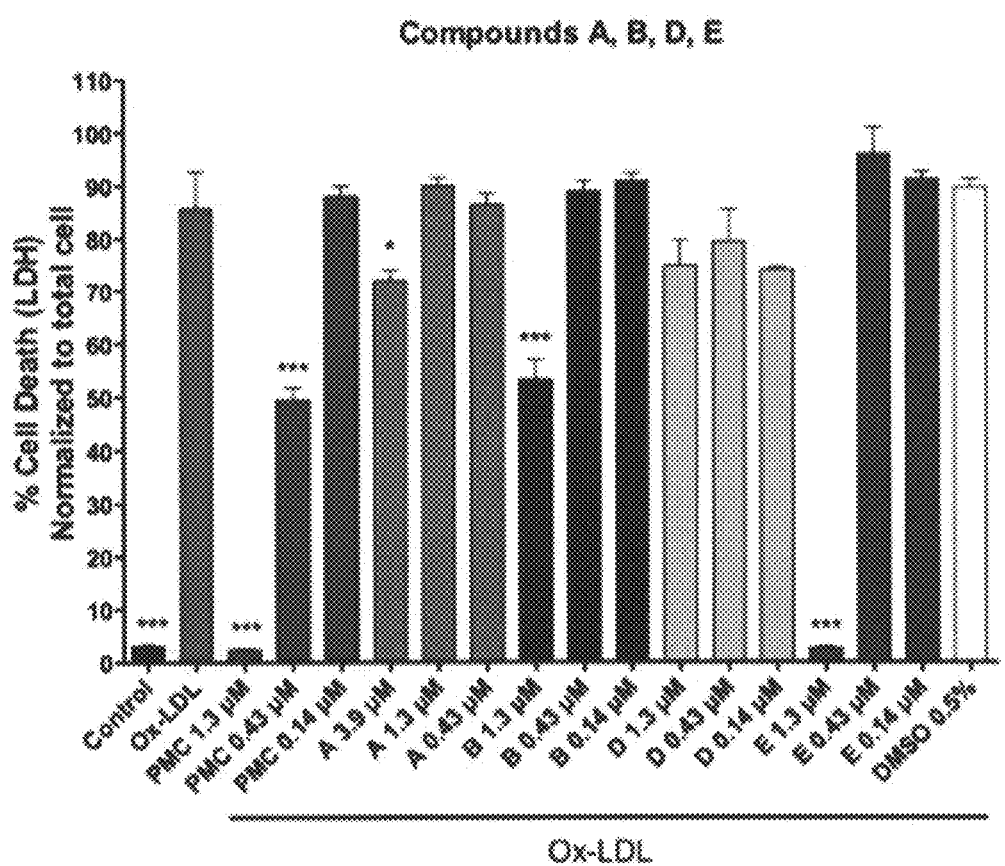
FIGS. 7B and 7C are graphs that show RPE protection by different experimental analogs of trolox and BHT. ARPE-19 cells were treated with ox-LDL (200 µg/ml) with and without different concentrations of the different analogs of trolox and BHT for 48 hours, cell death was determined by LDH assay. Note that many of the compounds were able to suppress ox-LDL-induced cell death similar to PMC. Data=mean±SEM, *$P<0.05$, ***$P<0.001$ compared to ox-LDL group, ANOVA.
Figure 7C:
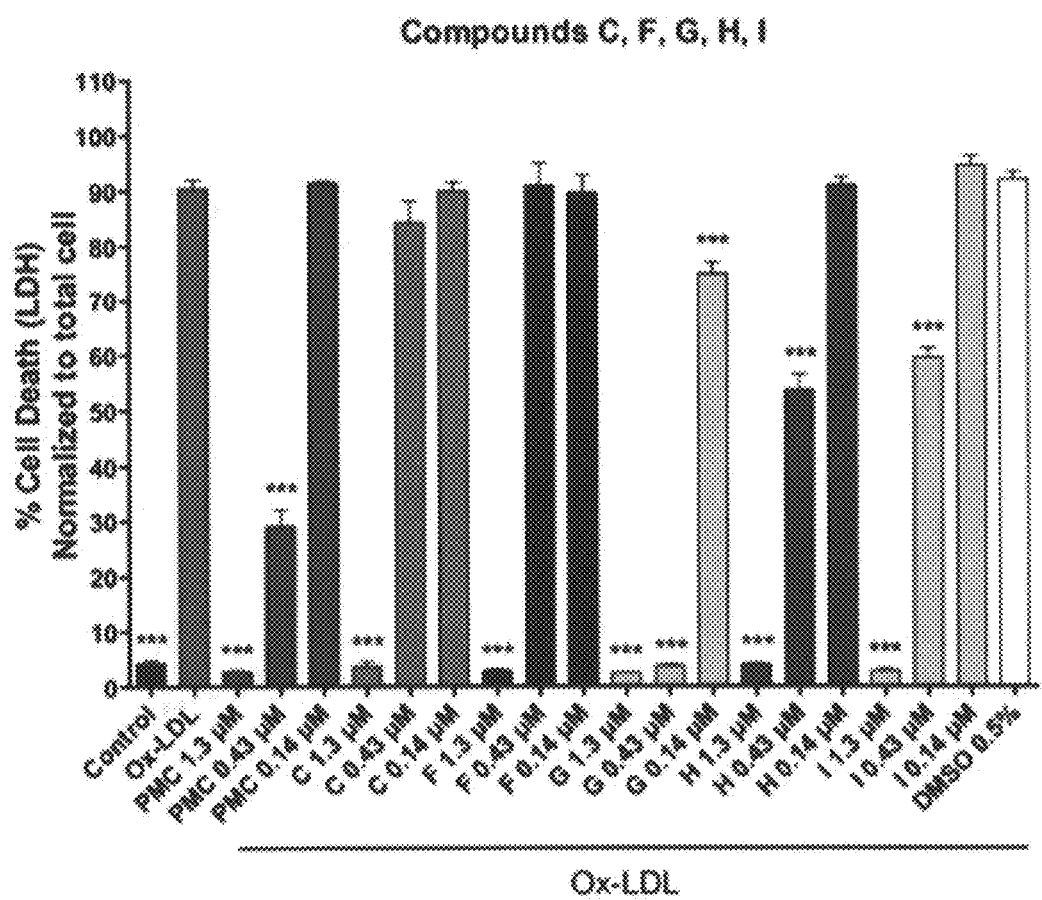

Without being bound by any theory, these data suggest that the hindered phenol group is uniquely effective in suppressing the detrimental effect of the ox-LDL in RPE, perhaps in part by suppressing ox-LDL-induced ROS formation but also possibly by an unknown mechanism. Furthermore, among the compounds with a hindered group, their RPE protective activities are also vastly different, for example PMC is significantly more potent than trolox and butylated hydroxyl toluene (BHT) (FIG. 5). Because of the association between hindered phenol group and RPE protection, experimental analogs derived from trolox and BHT were also tested, aiming at identifying more potent compounds. The data show that all the different analogs tested are more potent than the parental compounds (FIG. 7). In some embodiments, analogues of trolox and BHT disclosed herein are at least as potent as trolox and BHT at, e.g., protecting RPEs.

The use of anti-oxidants for various degenerative diseases including AMD has been proposed before, but they were primarily limited to dietary supplementation of various vitamins as a prophylaxis for AMD. In light of the findings from the screening experiments demonstrating the very potent RPE protective activity of trolox and BHT analogs, these specific classes of hindered phenol-containing anti-oxidants are also useful in mitigating the RPE damage and degeneration associated with dry AMD. In embodiments, highly potent analogs of trolox and/or BHT for RPE protection are provided herein. In embodiments, the analogs are selected based on the RPE protection assay. In embodiments, the RPE is directly exposed to the compound(s) by intraocular injection or periocular injection, or topical application in an animal. Alternatively, the compound or compounds are administered by systemic injection or infusion. In various embodiments, trolox and BHT analogs provided herein are based on RPE protection activity.

Materials and Methods

ARPE-19 cells: Human ARPE-19 cells (ATCC, Manassas, Va.) were propagated as described previously (Tseng, W. A., et al., Invest Ophthalmol Vis Sci, 2013. 54(1): p. 110-20). Cells were cultured in DMEMIF12 medium (Lonza, Walkersville, Md.) supplemented with 10% fetal bovine serum (FBS) (Atlanta Biologicals, Lawrenceville, Ga.), 2 mM L-glutamine (Lonza), and 100 U/ml penicillin–100 µg/ml streptomycin (Lonza) (complete media), and passaged at a ratio of 1:2 to 1:4 using trypsin-versene (Lonza). Prior to experiments, cells were maintained in 1% FBS medium for about 3 weeks to obtain ARPE-19 cells with differentiated phenotypes. The transepithelial electrical resistance (TER) of each batch of ARPE-19 cells was measured in cells cultured on laminin-coated 0.4 µm-pore transwell membranes (Corning, Mass.) to ensure it was at least 50 ohm·cm2 (EVOM2 Voltohmmeter, World Precision Instruments, Inc., Sarasota, Fla.) before the cells were used for experiments.

RPE protection assay and ROS measurement: The level of oxidation for each batch of ox-LDL was between 25-50 moles malondialdehyde/mg (MDA/mg) as measured by thiobarbituric acid reactive substances assay (TBAR) by the manufacturer (Alfa Aeser, Ward Hill, Mass.). RPE cells were serum starved for 18 to 24 hr, treated with ox-LDL at 200 µg/ml with and without various drugs at different concentrations. Cells were treated for 48 hr and levels of cell death were determined using the LDH release assay (CytoTox96 Non-Radioactive Cytotoxicity Assay, Promega, Madison, Wis.). The intracellular ROS for each treatment group at 12 to 48 hr were detected by using the ROS-ID® Total ROS detection kit (Enzo Life Sciences, Inc., Farmingdale, N.Y.) using a separate set of wells (TABLE 1).

TABLE 1

| Chembridge compound ID | CMPD ID | Structure | Protective activity against 200 µg/ml ox-LDL (% cell death, compound concentration) |
|---|---|---|---|
| 10176669 | J | 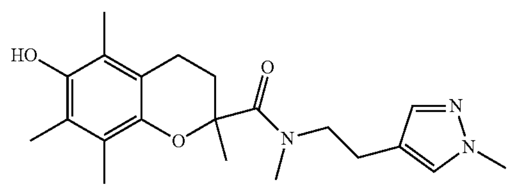 [SMILES: Cc1c(C)c2c(c(C)c1O)CCC(C)(C(=O)N(C)CCc1cnn(C)c1)O2] | <10%, 0.43 µM |
| 10643738 | M | 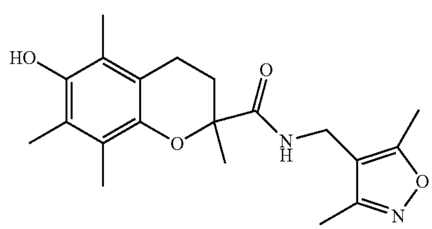 [SMILES: Cc1noc(C)c1CNC(=O)C1(C)CCc2c(C)c(O)c(C)c(C)c2O1] | <10%, 0.43 µM |
| 22716829 | P | 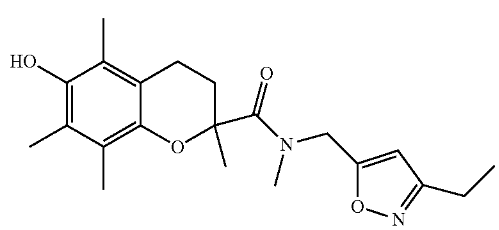 [SMILES: CCc1cc(CN(C)C(=O)C2(C)CCc3c(C)c(O)c(C)c(C)c3O2)on1] | <10%, 0.43 µM, ~60% 0.14 µM |
| 30465365 | S | 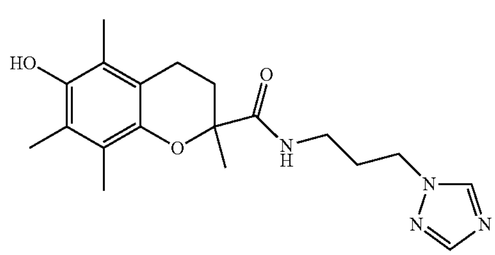 [SMILES: Cc1c(C)c2c(c(C)c1O)CCC(C)(C(=O)NCCCn1cncn1)O2] | <10%, 4.3 µM |

TABLE 1-continued

| Chembridge compound ID | CMPD ID | Structure | Protective activity against 200 μg/ml ox-LDL (% cell death, compound concentration) |
|---|---|---|---|
| 42034102 | K | 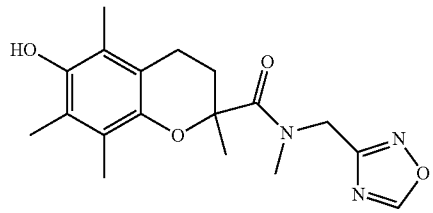 [SMILES: Cc1c(C)c2c(c(C)c1O)CCC(C)(C(=O)N(C)Cc1ncon1)O2] | <10%, 1.4 μM |
| 43995083 | N | 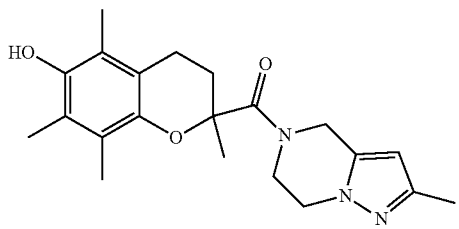 [SMILES: Cc1cc2n(n1)CCN(C(=O)C1(C)CCc3c(C)c(O)c(C)c(C)c3O1)C2] | <10%, 1.4 μM |
| 48380858 | Q | 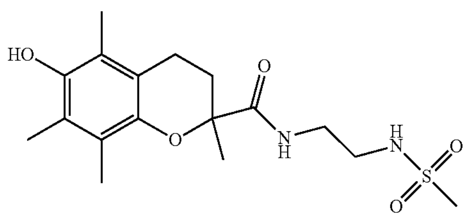 [SMILES: Cc1c(C)c2c(c(C)c1O)CCC(C)(C(=O)NCCNS(C)(=O)=O)O2] | <10%, 4.3 μM, ~50% 1.4 μM |
| 51451836 | T | 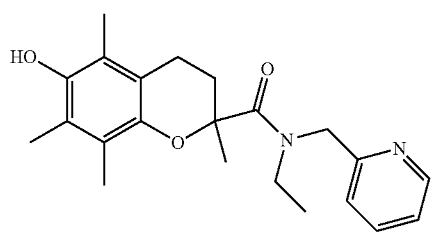 [SMILES: CCN(Cc1ccccn1)C(=O)C1(C)CCc2c(C)c(O)c(C)c(C)c2O1] | <10%, 1.4 μM |
| 52417666 | L | 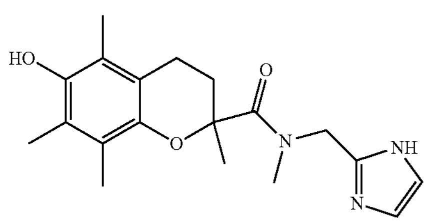 [SMILES: Cc1c(C)c2c(c(C)c1O)CCC(C)(C(=O)N(C)Cc1ncc[nH]1)O2] | <10%, 1.4 μM |
| 53999440 | O | 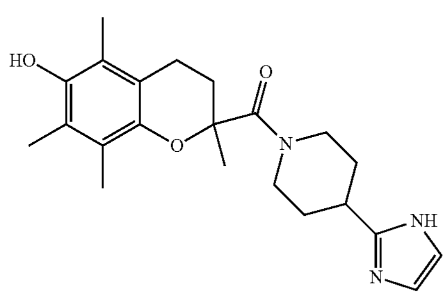 [SMILES: Cc1c(C)c2c(c(C)c1O)CCC(C)(C(=O)N1CCC(c3ncc[nH]3)CC1)O2] | <10%, 1.4 μM |

TABLE 1-continued

| Chembridge compound ID | CMPD ID | Structure | Protective activity against 200 μg/ml ox-LDL (% cell death, compound concentration) |
|---|---|---|---|
| 55761919 | R | 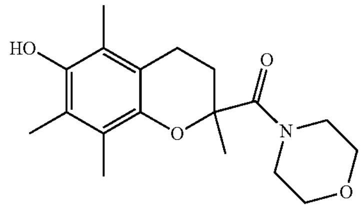 [SMILES: Cc1c(C)c2c(c(C)c1O)CCC(C)(C(=O)N1CCOCC1)O2] | <10%, 1.4 μM |
| 66079778 | U | 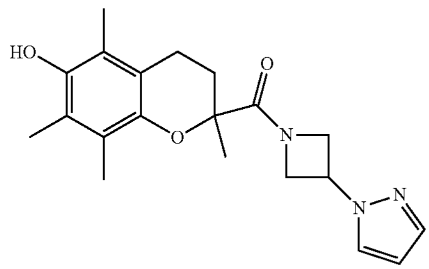 [SMILES: Cc1c(C)c2c(c(C)c1O)CCC(C)(C(=O)N1CC(n3cccn3)C1)O2] | <10%, 1.4 μM |
| 77448688 | V | 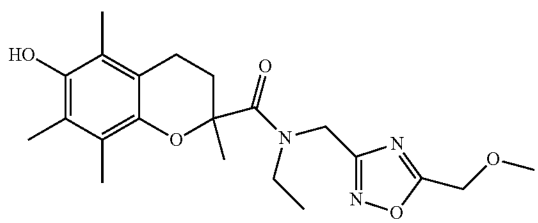 [SMILES: CCN(Cc1noc(COC)n1)C(=O)C1(C)CCc2c(C)c(O)c(C)c(C)c2O1] | <10%, 4.3 μM, ~30% 1.4 μM |
| 81930372 | W | 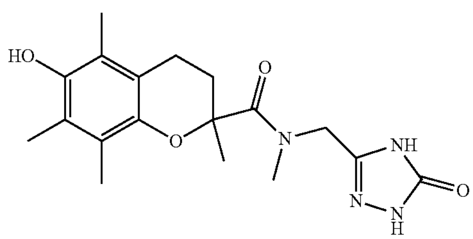 [SMILES: Cc1c(C)c2c(c(C)c1O)CCC(C)(C(=O)N(C)Cc1n[nH]c(=O)[nH]1)O2] | <12%, 1.4 μM |
| 83446338 | Y | 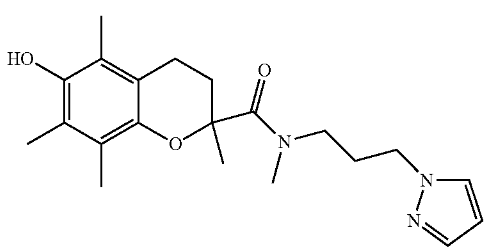 [SMILES: Cc1c(C)c2c(c(C)c1O)CCC(C)(C(=O)N(C)CCCn1cccn1)O2] | <21%, 4.3 μM, ~22% 1.4 μM |
| 84450719 | Z | 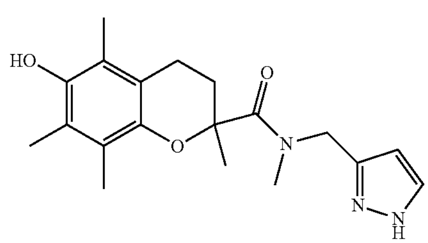 [SMILES: Cc1c(C)c2c(c(C)c1O)CCC(C)(C(=O)N(C)Cc1cc[nH]n1)O2] | <15%, 4.3 μM, ~22% 1.4 μM |

TABLE 1-continued

| Chembridge compound ID | CMPD ID | Structure | Protective activity against 200 μg/ml ox-LDL (% cell death, compound concentration) |
|---|---|---|---|
| 87998345 | X | 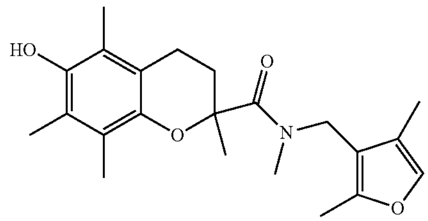 [SMILES: Cc1coc(C)c1CN(C)C(=O)C1(C)CCc2c(C)c(O)c(C)c(C)c2O1] | <16%, 4.3 μM, ~22% 1.4 μM |
| 95111309 | ZZ | 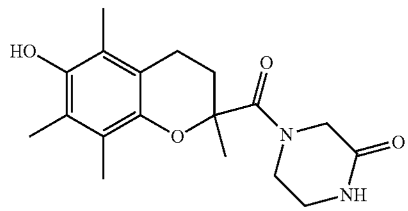 [SMILES: Cc1c(C)c2c(c(C)c1O)CCC(C)(C(=O)N1CCNC(=O)C1)O2] | <13%, 4.3 μM, ~23% 1.4 μM |

TABLE 1 displays the RPE protective activities against the cytotoxic effect of ox-LDL by the selected analogs tested and their molecular structures. ARPE-19 cells were treated with ox-LDL (200 μg/ml) with and without different concentrations of the selected analogs for 48 hours, cell death was determined by LDH assay. All the compounds tested in Table 1 significantly protected RPE cells from ox-LDL-induced cell death compared to no drug control (***P<0.001 for all, ANOVA).

Lysosomal integrity and NF-κB activation: ARPE-19 cells were treated with ox-LDL with and without different concentrations of trolox for 36 hours. Lysosomal integrity was determined by LysoTracker staining (ThermoFisher Scientific), followed by image analysis to quantify the number of intact lysosomes per cell. To measure activation of NF-κB, ARPE-19 cells were treated with 200 μg/ml ox-LDL with and without trolox for 36 hours, activation of NF-κB was detected by nuclear translocation of NF-κB p65 determined by immunostaining. Antibody specific for NF-κB p65 (Cell Signaling, Danvers, Mass.) was used for the immunostaining.

REFERENCES

Wang, L., et al., *Abundant lipid and protein components of drusen*. PLoS One, 2010. 5(4): p. e10329.

van Leeuwen, R., et al., *Epidemiology of age-related maculopathy: a review*. Eur J Epidemiol, 2003. 18(9): p. 845-54.

Barbosa, D. T., et al., *Age-related macular degeneration and protective effect of HMG Co-A reductase inhibitors (statins): results from the National Health and Nutrition Examination Survey 2005-2008*. Eye (Lond), 2014. 28(4): p. 472-80.

Sun, M., et al., *Light-induced oxidation of photoreceptor outer segment phospholipids generates ligands for CD36-mediated phagocytosis by retinal pigment epithelium: a potential mechanism for modulating outer segment phagocytosis under oxidant stress conditions*. J Biol Chem, 2006. 281(7): p. 4222-30.

Ishida, B. Y., et al., *High density lipoprotein mediated lipid efflux from retinal pigment epithelial cells in culture*. Br J Ophthalmol, 2006. 90(5): p. 616-20.

Curcio, C. A., et al., *The oil spill in ageing Bruch membrane*. Br J Ophthalmol, 2011. 95(12): p. 1638-45.

Curcio, C. A., et al., *Accumulation of cholesterol with age in human Bruch's membrane*. Invest Ophthalmol Vis Sci, 2001. 42(1): p. 265-74.

Krohne, T. U., et al., *Lipid peroxidation products reduce lysosomal protease activities in human retinal pigment epithelial cells via two different mechanisms of action*. Exp Eye Res, 2010. 90(2): p. 261-6.

Chen, H., et al., *Dysfunction of the retinal pigment epithelium with age: increased iron decreases phagocytosis and lysosomal activity*. Invest Ophthalmol Vis Sci, 2009. 50(4): p. 1895-902.

Jason Lim, W. L., Alan M Laties and Claire H Mitchell, *Age-dependent increases in lysosomal pH, lysosomal gene expression and autofluorescence of mouse RPE cells; parallels with the ABCA4−/− mice suggest causal factors in age dependent pathophysiology*, in *Invest Ophthalmol Vis Sci* 2014.

Sheedy, F. J., et al., *CD36 coordinates NLRP3 inflammasome activation by facilitating intracellular nucleation of soluble ligands into particulate ligands in sterile inflammation*. Nat Immunol, 2013. 14(8): p. 812-20.

Gnanaguru, G., et al., *Oxidized Lipoprotein Uptake Through the CD36 Receptor Activates the NLRP3 Inflammasome in Human Retinal Pigment Epithelial Cells*. Invest Ophthalmol Vis Sci, 2016. 57(11): p. 4704-12.

Tseng, W. A., et al., *NLRP3 inflammasome activation in retinal pigment epithelial cells by lysosomal destabilization: implications for age-related macular degeneration*. Invest Ophthalmol Vis Sci, 2013. 54(1): p. 110-20.

Ding, Z., et al., *Oxidant stress in mitochondrial DNA damage, autophagy and inflammation in atherosclerosis*. Sci Rep, 2013. 3: p. 1077.

Abais, J. M., et al., *Redox regulation of NLRP3 inflammasomes: ROS as trigger or effector?* Antioxid Redox Signal, 2015. 22(13): p. 1111-29.

Shaw, P. X., et al., *Oxidative stress, innate immunity, and age-related macular degeneration*. AIMS Mol Sci, 2016. 3(2): p. 196-221.

Petrilli, V., et al., *The inflammasome: a danger sensing complex triggering innate immunity*. Curr Opin Immunol, 2007. 19(6): p. 615-22.

Doyle, S. L., et al., *NLRP3 has a protective role in age-related macular degeneration through the induction of IL-18 by drusen components*. Nat Med, 2012. 18(5): p. 791-8.

Dodd, S., et al., *N-acetylcysteine for antioxidant therapy: pharmacology and clinical utility*. Expert Opin Biol Ther, 2008. 8(12): p. 1955-62.

Kikuchi, K., et al., *The free radical scavenger edaravone rescues rats from cerebral infarction by attenuating the release of high-mobility group box-1 in neuronal cells*. J Pharmacol Exp Ther, 2009. 329(3): p. 865-74.

Ledenev, A. N, et al., *A simple assay of the superoxide generation rate with Tiron as an EPR-visible radical scavenger*. Biochem Int, 1986. 13(2): p. 391-6.

Vorobjeva, N. V. and B. V. Pinegin, *Effects of the antioxidants Trolox, Tiron and Tempol on neutrophil extracellular trap formation*. Immunobiology, 2016. 221(2): p. 208-19.

Biewenga, G. P., G. R. Haenen, and A. Bast, *The pharmacology of the antioxidant lipoic acid*. Gen Pharmacol, 1997. 29(3): p. 315-31.

Ishizaki, N., et al., *Comparison of various lazaroid compounds for protection against ischemic liver injury*. Transplant Proc, 1997. 29(1-2): p. 1333-4.

Babich, H., *Butylated hydroxytoluene (BHT): a review*. Environ Res, 1982. 29(1): p. 1-29.

Cos, P., et al., *Comparative study of eight well-known polyphenolic antioxidants*. J Pharm Pharmacol, 2003. 55(9): p. 1291-7.

Guo, H., J. B. Callaway, and J. P. Ting, *Inflammasomes: mechanism of action, role in disease, and therapeutics*. Nat Med, 2015. 21(7): p. 677-87.

Coll, R. C., et al., *A small-molecule inhibitor of the NLRP3 inflammasome for the treatment of inflammatory diseases*. Nat Med, 2015. 21(3): p. 248-55.

Honda, H., et al., *Isoliquiritigenin is a potent inhibitor of NLRP3 inflammasome activation and diet-induced adipose tissue inflammation*. J Leukoc Biol, 2014. 96(6): p. 1087-100.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating or preventing or reducing age-related macular degeneration in a subject, the method comprising administering to the subject an effective amount of a compound having a formula (I),

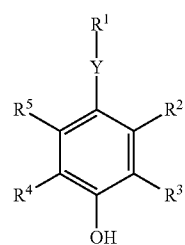

(I)

wherein:

Y is —O—;

$R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —$N(O)_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —NHC(O)$NR^{3A}R^{3B}$, —$N(O)_{m3}$, —$NR^{3A}R^{3B}$, —C(O)$R^{3C}$, —C(O)—$OR^{3C}$, —C(O)$NR^{3A}R^{3B}$, —$NR^{3A}SO_2R^{3D}$, —$NR^{3A}C(O)R^{3C}$, —$NR^{3A}C(O)OR^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —NHC(O)$NR^{4A}R^{4B}$, —$N(O)_{m4}$, —$NR^{4A}R^{4B}$, —C(O)$R^{4C}$, —C(O)—$OR^{4C}$, —C(O)$NR^{4A}R^{4B}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$CX^5_3$, —$CHX^5_2$, —$CH_2X^5$, —$OCX^5_3$, —$OCH_2X^5$, —$OCHX^5_2$, —CN, —$SO_{n5}R^{5D}$, —$SO_{v5}NR^{5A}R^{5B}$, —NHC(O)$NR^{5A}R^{5B}$, —$N(O)_{m5}$, —$NR^{5A}R^{5B}$, —C(O)$R^{5C}$, —C(O)—$OR^{5C}$, —C(O)$NR^{5A}R^{5B}$, —$NR^{5A}SO_2R^{5D}$, —$NR^{5A}C(O)R^{5C}$, —$NR^{5A}C(O)OR^{5C}$, —$NR^{5A}OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{13}$, $R^{14}$ and $R^{15}$ is independently hydrogen, substituted or unsubstituted alkyl, I substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, and $R^{5D}$ is independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ together with atoms attached thereto are optionally joined to form substituted or unsubstituted cycloalkyl, substituted or unsubstituted heterocycloalkyl, substituted or unsubstituted aryl or substituted or unsubstituted heteroaryl;

n1, n2, n3, n4, and n5 are independently an integer from 0 to 4;

m1, m2, m3, m4, m5, v1, v2, v3, v4, and v5 are independently an integer from 1 to 2; and X, $X^1$, $X^2$, $X^3$, $X^4$, and $X^5$ are independently —F, —Cl, —Br, or —I, or a pharmaceutically acceptable salt thereof.

2. The method of claim 1, having the formula:

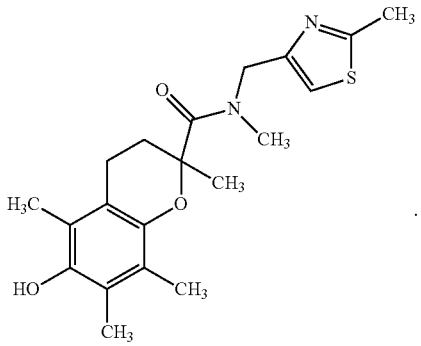

3. The method of claim 1, wherein Y is —O—; and/or $R^1$ is hydrogen, or substituted or unsubstituted $C_1$-$C_4$ alkyl.

4. The method of claim 1, wherein $R^2$ and $R^5$ are independently hydrogen or unsubstituted $C_1$-$C_4$ alkyl; and/or $R^3$ and $R^4$ are independently hydrogen, or substituted or unsubstituted $C_1$-$C_4$ alkyl.

5. The method of claim 1, wherein the compound has a formula (II),

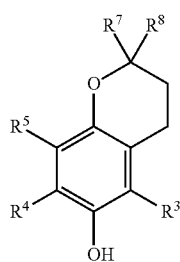

wherein:

$R^7$ is hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —NHC(O)$NR^{7A}R^{7B}$, —N(O)$_{m7}$, —$NR^{7A}R^{7B}$, —C(O)$R^{7C}$, —C(O)—$OR^{7C}$, —C(O)$NR^{7A}R^{7B}$, —$OR^{7D}$, —$NR^{7A}SO_2R^{7D}$, —$NR^{7A}C(O)R^{7D}$, —$NR^{7A}C(O)OR^{7C}$, —$NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, —$CX^8_3$, —$CHX^8_2$, —$CH_2X^8$, —$OCX^8_3$, —$OCH_2X^8$, —$OCHX^8_2$, —CN, —$SO_{n8}R^{8D}$, —$SO_{v8}NR^{8A}R^{8B}$, —NHC(O)$NR^{8A}R^{8B}$, —N(O)$_{m8}$, —$NR^{8A}R^{8B}$, —C(O)$R^{8C}$, —C(O)—$OR^{8C}$, —C(O)$NR^{8A}R^{8B}$, —$OR^{8D}$, —$NR^{8A}SO_2R^{8D}$, —$NR^{8A}C(O)R^{8C}$, —$NR^{8A}C(O)OR^{8C}$, —$NR^{8A}OR^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{7A}$, $R^{7B}$, $R^{7C}$, $R^{7D}$, $R^{8A}$, $R^{8B}$, $R^{8C}$, and $R^{8D}$ is independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n7 and n8 are independently an integer from 0 to 4;

m7, m8, v7 and v8 are independently an integer from 1 to 2; and $X^7$, and $X^8$ are independently —F, —Cl, —Br, or —I.

6. The method of claim 5, wherein $R^7$ is hydrogen, or unsubstituted $C_1$-$C_4$ alkyl; and/or $R^8$ is represented as:

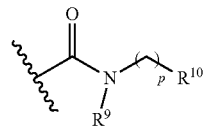

wherein:

p is an integer from 0 to 4;

each $R^9$ and $R^{10}$ is independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^9$ and $R^{10}$ together with atoms attached thereto are optionally joined to form substituted or unsubstituted cycloalkyl, substituted or unsubstituted heterocycloalkyl, substituted or unsubstituted aryl or substituted or unsubstituted heteroaryl.

7. The method of claim 6, wherein $R^9$ is hydrogen or unsubstituted $C_1$-$C_4$ alkyl; and/or $R^{10}$ is

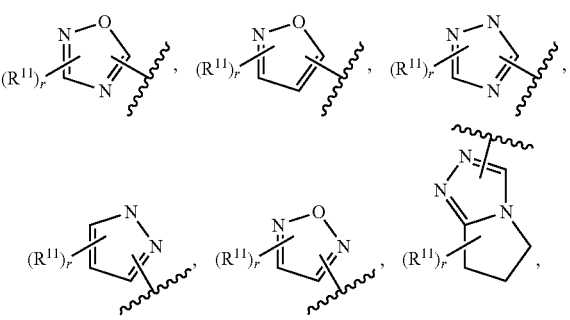

-continued

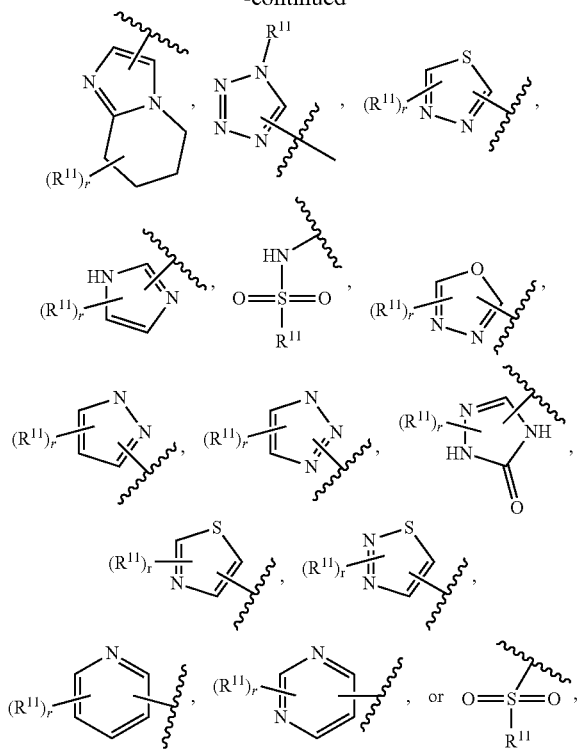

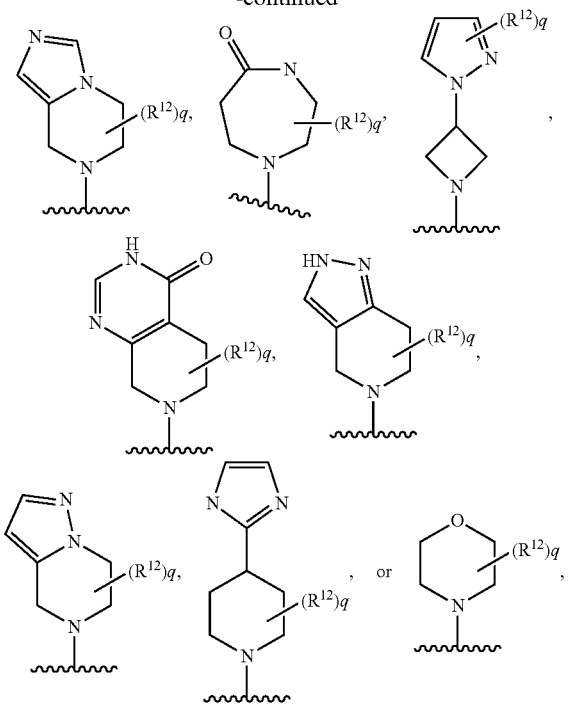

wherein $R^{11}$ is hydrogen, halogen, —$CX^{11}_3$, —$CHX^{11}_2$, —$CH_2X^{11}$, —$OCX^{11}_3$, —$OCH_2X^{11}$, —$OCHX^{11}_2$, —CN, —$SO_{n11}R^{11D}$, —$SO_{v11}NR^{11A}R^{11B}$, —NHC(O)$NR^{11A}R^{11B}$, —$NR^{11A}R^{11B}$, —$C(O)R^{11C}$, —C(O)$OR^{11C}$, —$C(O)NR^{11A}R^{11B}$, —$OR^{11D}$, —$NR^{11A}SO_2R^{11D}$, —$NR^{11A}C(O)R^{11C}$, —$NR^{11A}C(O)OR^{11C}$, —$NR^{11A}OR^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{11A}$, $R^{11B}$, $R^{11C}$, and $R^{11D}$ is independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n11 is an integer from 0 to 4;

m11 is an integer from 1 to 2;

r is an integer from 0 to 9; and $X^{11}$ is —F, —Cl, —Br, or —I.

8. The method of claim 7, wherein $R^{11}$ is hydrogen or unsubstituted $C_1$-$C_4$ alkyl.

9. The method of claim 5, wherein $R^9$ and $R^{10}$ together with the nitrogen attached thereto are joined to form:

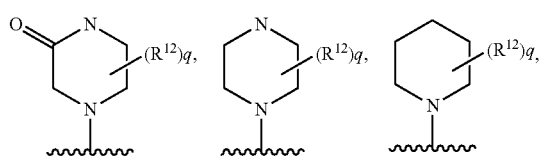

wherein $R^{12}$ is hydrogen, halogen, —$CX^{12}_3$, —$CHX^{12}_2$, —$CH_2X^{12}$, —$OCX^{12}_3$, —$OCH_2X^{12}$, —$OCHX^{12}_2$, —CN, —$SO_{n12}R^{12D}$, —$SO_{v12}NR^{12A}R^{12B}$, —NHC(O)$NR^{12A}R^{12B}$, —$N(O)_{m12}$, —$NR^{12A}R^{12B}$, —$C(O)R^{12C}$, —C(O)—$OR^{12C}$, —$C(O)NR^{12A}R^{12B}$, —$OR^{12D}$, —$NR^{12A}SO_2R^{12D}$, —$NR^{12A}C(O)R^{12C}$, —$NR^{12A}C(O)OR^{12C}$, —$NR^{12A}OR^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{12A}$, $R^{12B}$, $R^{12C}$, and $R^{12D}$ is independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n12 is an integer from 0 to 4;

m12 is an integer from 1 to 2;

q is an integer from 0 to 6; and $X^{12}$ is —F, —Cl, —Br, or —I.

10. The method of claim 9, wherein $R^{12}$ is hydrogen, unsubstituted $C_1$-$C_4$ alkyl, —OH, —$OCH_3$, —$CH_2OH$ or —$CH_2CH_2OH$.

11. The method of claim 1, wherein the compound is:

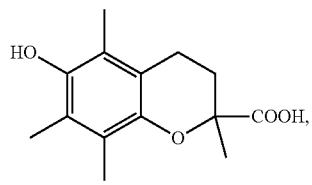

69
-continued
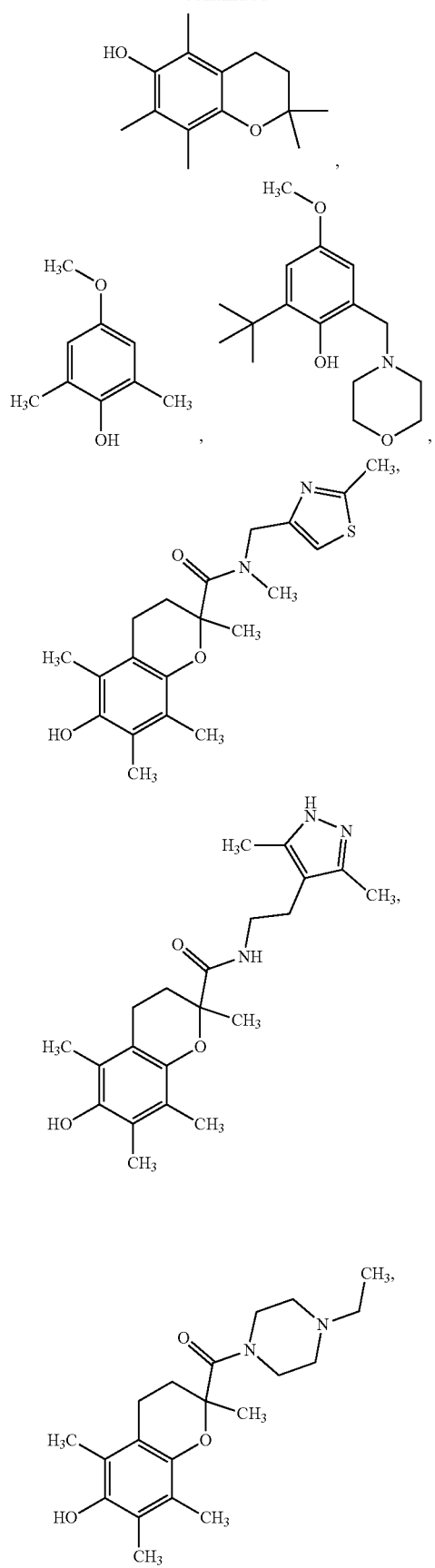
70
-continued
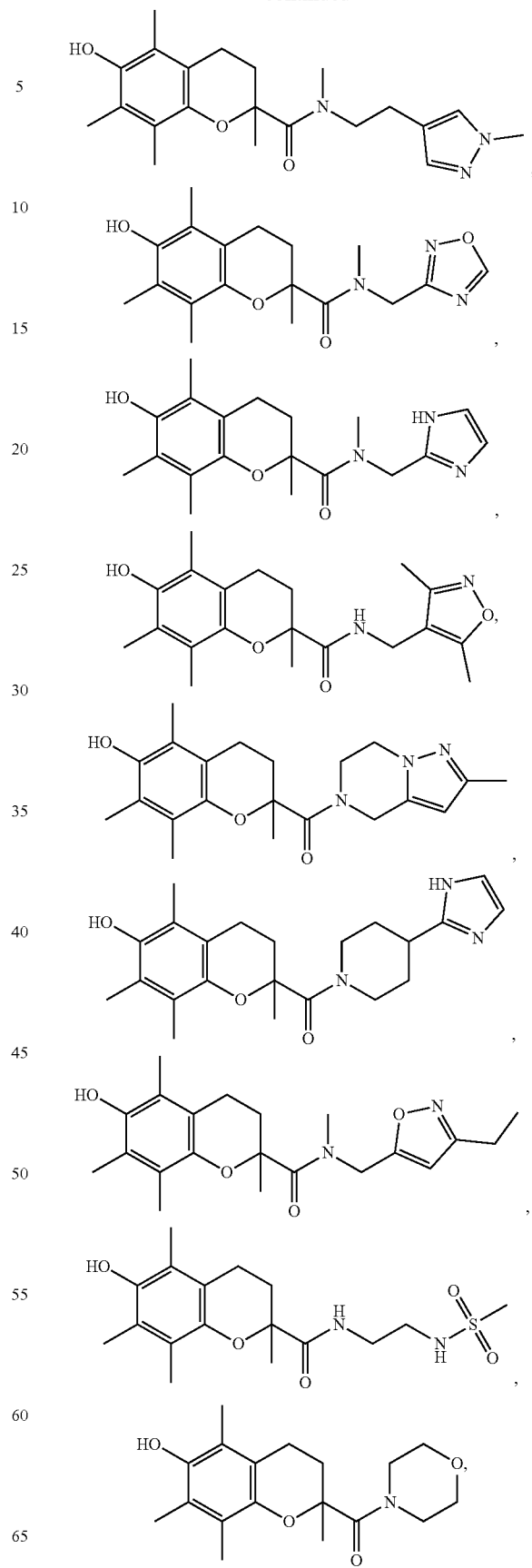

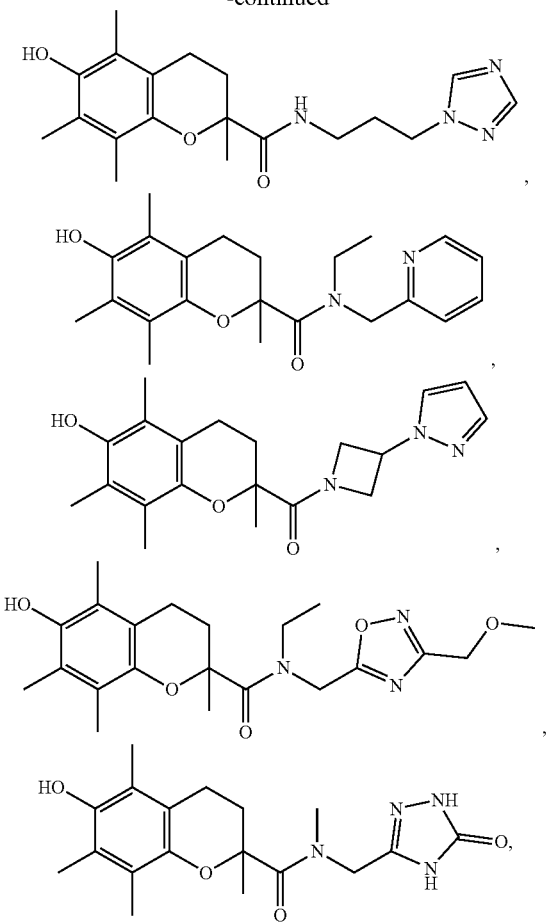
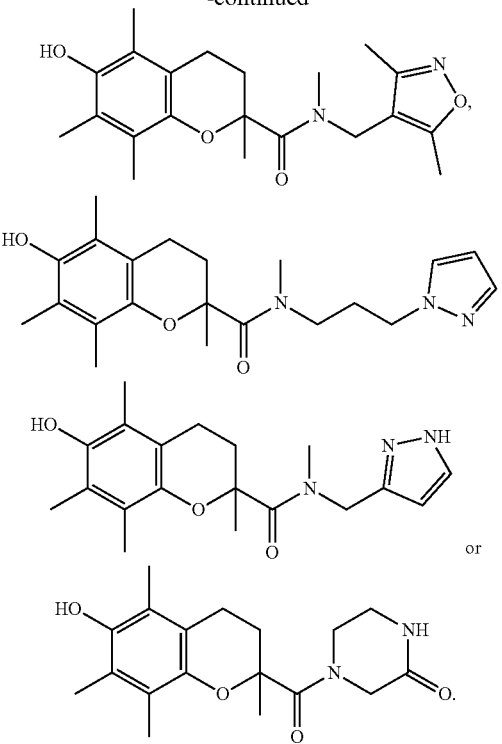
12. The method of claim 1, wherein the age-related macular degeneration comprises retinal pigment epithelium (RPE) degeneration or geography atrophy (GA).
13. The method of claim 1, wherein the compound is administered by intraocular injection or topically.